United States Patent
Orr et al.

(10) Patent No.: US 11,000,428 B2
(45) Date of Patent: May 11, 2021

(54) THREE-DIMENSIONAL SUBSTRATE COMPRISING A TISSUE LAYER

(71) Applicant: The Procter & Gamble Company, Cincinnati, OH (US)

(72) Inventors: Jill Marlene Orr, Liberty Township, OH (US); Rodrigo Rosati, Frankfurt am Main (DE); Adrien Grenier, Frankfurt am Main (DE); Aniruddha Chatterjee, Kelkheim (DE); Darrell Ian Brown, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 751 days.

(21) Appl. No.: 15/453,997

(22) Filed: Mar. 9, 2017

(65) Prior Publication Data
US 2017/0258647 A1 Sep. 14, 2017

Related U.S. Application Data

(60) Provisional application No. 62/306,676, filed on Mar. 11, 2016.

(51) Int. Cl.
*A61F 13/511* (2006.01)
*B32B 5/26* (2006.01)
(Continued)

(52) U.S. Cl.
CPC .... *A61F 13/51104* (2013.01); *A61F 13/5116* (2013.01); *A61F 13/53* (2013.01);
(Continued)

(58) Field of Classification Search
CPC ............ A61F 13/51104; A61F 13/5116; A61F 13/53; A61F 2013/51092; A61F 2013/530481
See application file for complete search history.

(56) References Cited

U.S. PATENT DOCUMENTS

| 3,301,746 A | 1/1967 | Sanford et al. |
|---|---|---|
| 3,323,983 A | 6/1967 | Palmer et al. |

(Continued)

FOREIGN PATENT DOCUMENTS

| EP | 0 617 164 B1 | 8/1997 |
|---|---|---|
| EP | 1 876 291 A2 | 1/2005 |

(Continued)

OTHER PUBLICATIONS

US 5,972,466 A, 10/1999, Trokhan (withdrawn)
(Continued)

*Primary Examiner* — Kai H Weng
(74) *Attorney, Agent, or Firm* — William E. Gallagher

(57) ABSTRACT

A three-dimensional substrate has a first surface, a second surface, land areas and comprises three-dimensional protrusions extending outward from the second surface of the three-dimensional substrate. The three-dimensional protrusions are surrounded by the land areas. The three-dimensional substrate is a laminate comprising at least two layers in a face to face relationship. The second layer comprise a tissue layer facing outward from the second surface of the three-dimensional substrate. The tissue layer comprises at least 80% pulp fibers by weight of the tissue layer.

16 Claims, 16 Drawing Sheets

(51) Int. Cl.

| | | |
|---|---|---|
| B32B 3/26 | (2006.01) | |
| B32B 7/02 | (2019.01) | |
| B32B 3/08 | (2006.01) | |
| B32B 7/12 | (2006.01) | |
| B32B 5/16 | (2006.01) | |
| B32B 7/04 | (2019.01) | |
| B32B 21/13 | (2006.01) | |
| B32B 23/10 | (2006.01) | |
| B32B 5/30 | (2006.01) | |
| B32B 21/08 | (2006.01) | |
| B32B 23/08 | (2006.01) | |
| B32B 3/04 | (2006.01) | |
| B32B 27/12 | (2006.01) | |
| B32B 21/10 | (2006.01) | |
| B32B 23/04 | (2006.01) | |
| A61F 13/53 | (2006.01) | |
| B32B 3/30 | (2006.01) | |
| B32B 5/02 | (2006.01) | |
| B32B 29/02 | (2006.01) | |
| D04H 3/007 | (2012.01) | |
| D04H 3/011 | (2012.01) | |
| D04H 3/16 | (2006.01) | |
| D06C 23/04 | (2006.01) | |
| D21H 27/00 | (2006.01) | |
| A61F 13/51 | (2006.01) | |

(52) U.S. Cl.
CPC .......... *B32B 3/04* (2013.01); *B32B 3/08* (2013.01); *B32B 3/26* (2013.01); *B32B 3/266* (2013.01); *B32B 3/30* (2013.01); *B32B 5/022* (2013.01); *B32B 5/16* (2013.01); *B32B 5/26* (2013.01); *B32B 5/30* (2013.01); *B32B 7/02* (2013.01); *B32B 7/04* (2013.01); *B32B 7/12* (2013.01); *B32B 21/08* (2013.01); *B32B 21/10* (2013.01); *B32B 21/13* (2013.01); *B32B 23/04* (2013.01); *B32B 23/044* (2013.01); *B32B 23/08* (2013.01); *B32B 23/10* (2013.01); *B32B 27/12* (2013.01); *B32B 29/02* (2013.01); *D04H 3/007* (2013.01); *D04H 3/011* (2013.01); *D04H 3/16* (2013.01); *D06C 23/04* (2013.01); *D21H 27/002* (2013.01); *A61F 2013/51092* (2013.01); *A61F 2013/530481* (2013.01); *B32B 2250/02* (2013.01); *B32B 2250/03* (2013.01); *B32B 2250/05* (2013.01); *B32B 2250/20* (2013.01); *B32B 2260/02* (2013.01); *B32B 2260/021* (2013.01); *B32B 2260/048* (2013.01); *B32B 2262/0223* (2013.01); *B32B 2262/0246* (2013.01); *B32B 2262/0253* (2013.01); *B32B 2262/0261* (2013.01); *B32B 2262/0276* (2013.01); *B32B 2262/0284* (2013.01); *B32B 2262/04* (2013.01); *B32B 2262/062* (2013.01); *B32B 2262/065* (2013.01); *B32B 2262/067* (2013.01); *B32B 2262/08* (2013.01); *B32B 2262/12* (2013.01); *B32B 2262/14* (2013.01); *B32B 2264/02* (2013.01); *B32B 2307/402* (2013.01); *B32B 2307/41* (2013.01); *B32B 2307/50* (2013.01); *B32B 2307/546* (2013.01); *B32B 2307/718* (2013.01); *B32B 2307/72* (2013.01); *B32B 2307/726* (2013.01); *B32B 2307/728* (2013.01); *B32B 2307/7265* (2013.01); *B32B 2555/02* (2013.01); *D10B 2509/026* (2013.01)

(56) References Cited

U.S. PATENT DOCUMENTS

| | | |
|---|---|---|
| 3,700,623 A | 10/1972 | Keim |
| 3,772,076 A | 11/1973 | Keim |
| 3,974,025 A | 8/1976 | Ayers |
| 3,994,771 A | 11/1976 | Morgan, Jr. et al. |
| 4,011,389 A | 3/1977 | Langdon |
| 4,191,609 A | 3/1980 | Trokhan |
| 4,191,756 A | 3/1980 | Masi et al. |
| 4,300,981 A | 11/1981 | Carstens |
| 4,391,878 A | 7/1983 | Drach |
| 4,440,597 A | 4/1984 | Wells et al. |
| 4,514,345 A | 4/1985 | Johnson et al. |
| 4,528,239 A | 7/1985 | Trokhan |
| 4,529,480 A | 7/1985 | Trokhan |
| 4,557,801 A | 12/1985 | Avis |
| 4,637,859 A | 1/1987 | Trokhan |
| 4,795,453 A | 1/1989 | Wolfe |
| 4,935,021 A | 6/1990 | Huffman |
| 5,059,282 A | 10/1991 | Ampulski et al. |
| 5,059,283 A | 10/1991 | Hood et al. |
| 5,073,235 A | 12/1991 | Trokhan |
| 5,098,522 A | 3/1992 | Smurkoski et al. |
| 5,151,092 A | 9/1992 | Buell et al. |
| 5,164,046 A | 11/1992 | Ampulski et al. |
| 5,217,445 A | 6/1993 | Young |
| 5,221,435 A | 6/1993 | Smith, Jr. |
| 5,245,025 A | 9/1993 | Trokhan |
| 5,246,545 A | 9/1993 | Ampulski et al. |
| 5,246,546 A | 9/1993 | Ampulski |
| 5,260,171 A | 11/1993 | Smurkoski et al. |
| 5,275,700 A | 1/1994 | Trokhan |
| 5,277,761 A | 1/1994 | Van Phan et al. |
| 5,294,475 A | 3/1994 | Mcneil |
| 5,328,565 A | 7/1994 | Rasch et al. |
| 5,334,289 A | 8/1994 | Trokhan et al. |
| 5,364,504 A | 11/1994 | Smurkoski et al. |
| 5,366,785 A | 11/1994 | Sawdai |
| 5,383,869 A | 1/1995 | Osborn, III |
| 5,401,267 A | 3/1995 | Couture-Dorschner et al. |
| 5,411,636 A | 5/1995 | Hermans et al. |
| 5,431,786 A | 7/1995 | Rasch et al. |
| 5,443,691 A | 8/1995 | Phan et al. |
| 5,468,323 A | 11/1995 | Mcneil |
| 5,496,624 A | 3/1996 | Stelljes, Jr. et al. |
| 5,500,277 A | 3/1996 | Trokhan et al. |
| 5,503,715 A | 4/1996 | Trokhan et al. |
| 5,509,914 A | 4/1996 | Osborn, III |
| 5,514,523 A | 5/1996 | Trokhan et al. |
| 5,520,778 A | 5/1996 | Sawdai |
| 5,527,428 A | 6/1996 | Trokhan et al. |
| 5,529,664 A | 6/1996 | Trokhan et al. |
| 5,534,326 A | 7/1996 | Trokhan et al. |
| 5,549,790 A | 8/1996 | Van Phan |
| 5,552,345 A | 9/1996 | Schrantz et al. |
| 5,554,467 A | 9/1996 | Trokhan et al. |
| 5,556,509 A | 9/1996 | Trokhan et al. |
| 5,562,645 A | 10/1996 | Tanzer et al. |
| 5,566,724 A | 10/1996 | Trokhan et al. |
| 5,575,786 A | 11/1996 | Osborn, III |
| 5,580,423 A | 12/1996 | Ampulski et al. |
| 5,599,335 A | 2/1997 | Goldman et al. |
| 5,609,725 A | 3/1997 | Van Phan |
| 5,614,061 A | 3/1997 | Van Phan et al. |
| 5,624,790 A | 4/1997 | Trokhan et al. |
| 5,628,876 A | 5/1997 | Ayers et al. |
| 5,629,052 A | 5/1997 | Trokhan et al. |
| 5,637,194 A | 6/1997 | Ampulski et al. |
| 5,654,076 A | 8/1997 | Trokhan et al. |
| 5,656,132 A | 8/1997 | Farrington, Jr. et al. |
| 5,674,663 A | 10/1997 | McFarland et al. |
| 5,679,222 A | 10/1997 | Rasch et al. |
| 5,693,187 A | 12/1997 | Ampulski et al. |
| 5,693,406 A | 12/1997 | Wegele et al. |
| 5,709,775 A | 1/1998 | Trokhan et al. |
| 5,714,041 A | 2/1998 | Ayers et al. |
| 5,716,692 A | 2/1998 | Warner et al. |

(56) References Cited

U.S. PATENT DOCUMENTS

| | | |
|---|---|---|
| 5,718,806 A | 2/1998 | Trokhan et al. |
| 5,728,268 A | 3/1998 | Weisman et al. |
| 5,741,402 A | 4/1998 | Trokhan et al. |
| 5,744,007 A | 4/1998 | Trokhan et al. |
| 5,776,307 A | 7/1998 | Ampulski et al. |
| 5,776,311 A | 7/1998 | Trokhan et al. |
| 5,776,312 A | 7/1998 | Trokhan et al. |
| 5,779,860 A | 7/1998 | Hollenberg et al. |
| 5,795,440 A | 8/1998 | Ampulski et al. |
| 5,804,036 A | 9/1998 | Phan et al. |
| 5,804,281 A | 9/1998 | Phan et al. |
| 5,814,190 A | 9/1998 | Van Phan |
| 5,817,377 A | 10/1998 | Trokhan et al. |
| 5,820,730 A | 10/1998 | Phan et al. |
| 5,830,558 A | 11/1998 | Barnholtz |
| 5,832,362 A | 11/1998 | Trokhan |
| 5,837,103 A | 11/1998 | Trokhan et al. |
| 5,840,403 A | 11/1998 | Trokhan et al. |
| 5,840,411 A | 11/1998 | Stelljes, Jr. et al. |
| 5,843,279 A | 12/1998 | Phan et al. |
| 5,846,379 A | 12/1998 | Ampulski et al. |
| 5,855,738 A | 1/1999 | Weisman et al. |
| 5,855,739 A | 1/1999 | Ampulski et al. |
| 5,858,554 A | 1/1999 | Neal et al. |
| 5,861,082 A | 1/1999 | Ampulski et al. |
| 5,865,950 A | 2/1999 | Vinson et al. |
| 5,871,887 A | 2/1999 | Trokhan et al. |
| 5,885,421 A | 3/1999 | Ensign et al. |
| 5,893,965 A | 4/1999 | Trokhan et al. |
| 5,895,623 A | 4/1999 | Trokhan et al. |
| 5,897,745 A | 4/1999 | Ampulski et al. |
| 5,900,122 A | 5/1999 | Huston |
| 5,904,811 A | 5/1999 | Ampulski et al. |
| 5,906,710 A | 5/1999 | Trokhan |
| 5,906,711 A | 5/1999 | Barnholtz |
| 5,919,556 A | 7/1999 | Barnholtz |
| 5,935,381 A | 8/1999 | Trokhan et al. |
| 5,938,893 A | 8/1999 | Trokhan et al. |
| 5,942,085 A | 8/1999 | Neal et al. |
| 5,948,210 A | 9/1999 | Huston |
| 5,951,537 A | 9/1999 | Osborn, III |
| 5,954,097 A | 9/1999 | Boutilier |
| 5,962,860 A | 10/1999 | Trokhan et al. |
| 5,972,813 A | 10/1999 | Polat et al. |
| 5,980,691 A | 11/1999 | Weisman et al. |
| 6,010,598 A | 1/2000 | Boutilier et al. |
| 6,030,690 A | 2/2000 | Mcneil et al. |
| 6,039,839 A | 3/2000 | Trokhan et al. |
| 6,048,938 A | 4/2000 | Neal et al. |
| 6,074,525 A | 6/2000 | Richards |
| 6,086,715 A | 7/2000 | Mcneil |
| 6,090,241 A | 7/2000 | Trokhan et al. |
| 6,099,781 A | 8/2000 | Ampulski |
| 6,103,062 A | 8/2000 | Ampulski et al. |
| 6,103,067 A | 8/2000 | Stelljes, Jr. et al. |
| 6,103,953 A | 8/2000 | Cree |
| 6,106,670 A | 8/2000 | Weisman et al. |
| 6,110,324 A | 8/2000 | Trokhan et al. |
| 6,113,723 A | 9/2000 | Mcneil et al. |
| 6,117,270 A | 9/2000 | Trokhan |
| 6,117,525 A | 9/2000 | Trokhan et al. |
| 6,136,146 A | 10/2000 | Phan et al. |
| 6,139,686 A | 10/2000 | Trokhan et al. |
| 6,149,849 A | 11/2000 | Ampulski |
| 6,165,319 A | 12/2000 | Heath et al. |
| 6,171,447 B1 | 1/2001 | Trokhan |
| 6,187,138 B1 | 2/2001 | Neal et al. |
| 6,193,839 B1 | 2/2001 | Ampulski et al. |
| 6,193,847 B1 | 2/2001 | Trokhan |
| 6,200,419 B1 | 3/2001 | Phan |
| 6,210,644 B1 | 4/2001 | Trokhan et al. |
| 6,238,682 B1 | 5/2001 | Klofta et al. |
| 6,251,331 B1 | 6/2001 | Ampulski et al. |
| 6,258,516 B1 | 7/2001 | Trokhan et al. |
| 6,271,532 B1 | 8/2001 | Trokhan et al. |
| 6,273,996 B1 | 8/2001 | Hollenberg et al. |
| 6,287,425 B1 | 9/2001 | Richards |
| 6,287,641 B1 | 9/2001 | Ostendorf et al. |
| 6,296,862 B1 | 10/2001 | Paul |
| 6,329,565 B1 | 12/2001 | Dutkiewicz et al. |
| 6,344,241 B1 | 2/2002 | Ampulski |
| 6,358,030 B1 | 3/2002 | Ampulski |
| 6,358,594 B1 | 3/2002 | Ampulski |
| 6,368,465 B1 | 4/2002 | Stelljes, Jr. et al. |
| 6,420,013 B1 | 7/2002 | Vinson et al. |
| 6,420,100 B1 | 7/2002 | Trokhan et al. |
| 6,423,186 B1 | 7/2002 | Trokhan et al. |
| 6,432,272 B1 | 8/2002 | Hollenberg et al. |
| 6,458,447 B1 | 10/2002 | Cabell et al. |
| 6,464,831 B1 | 10/2002 | Trokhan et al. |
| 6,500,307 B2 | 12/2002 | Richards |
| 6,540,880 B1 | 4/2003 | Trokhan et al. |
| 6,551,453 B2 | 4/2003 | Weisman et al. |
| 6,554,601 B2 | 4/2003 | Ampulski et al. |
| 6,561,781 B1 | 5/2003 | Ampulski |
| 6,576,090 B1 | 6/2003 | Trokhan et al. |
| 6,576,091 B1 | 6/2003 | Cabell et al. |
| 6,660,129 B1 | 12/2003 | Cabell et al. |
| 6,673,202 B2 | 1/2004 | Burazin et al. |
| 6,706,152 B2 | 3/2004 | Burzain et al. |
| 6,733,833 B2 | 5/2004 | Ampulski |
| 6,743,571 B1 | 6/2004 | Hill et al. |
| 6,746,570 B2 | 6/2004 | Burzain et al. |
| 6,746,766 B2 | 6/2004 | Bond et al. |
| 6,749,719 B2 | 6/2004 | Burzain et al. |
| 6,787,000 B2 | 9/2004 | Burzain et al. |
| 6,790,314 B2 | 9/2004 | Burzain et al. |
| 6,797,114 B2 | 9/2004 | Hu |
| 6,802,937 B2 | 10/2004 | Johnston et al. |
| 6,808,790 B2 | 10/2004 | Chen et al. |
| 6,821,385 B2 | 11/2004 | Burzain et al. |
| 6,821,386 B2 | 11/2004 | Weisman et al. |
| 6,860,970 B2 | 3/2005 | Ampulski |
| 6,890,872 B2 | 5/2005 | Bond et al. |
| 6,913,859 B2 | 7/2005 | Hill et al. |
| 6,946,506 B2 | 9/2005 | Bond et al. |
| 7,094,320 B1 | 8/2006 | Phan |
| 7,118,647 B2 | 10/2006 | Cabell et al. |
| 7,128,809 B2 | 10/2006 | Vinson et al. |
| 7,265,067 B1 | 9/2007 | Phan |
| 7,311,800 B2 | 12/2007 | Russell et al. |
| 7,374,638 B2 | 5/2008 | Horenziak et al. |
| 7,374,639 B2 | 5/2008 | Ampulski et al. |
| 7,419,569 B2 | 9/2008 | Hermans et al. |
| 7,494,563 B2 | 2/2009 | Edwards et al. |
| RE40,724 E | 6/2009 | Barnholtz |
| 7,744,576 B2 | 1/2010 | Busam et al. |
| 7,687,140 B2 | 3/2010 | Manifold et al. |
| 7,691,229 B2 | 4/2010 | Vinson et al. |
| 7,704,601 B2 | 4/2010 | Manifold et al. |
| 7,741,234 B2 | 6/2010 | Smith et al. |
| 7,744,723 B2 | 6/2010 | Sheehan et al. |
| 7,750,203 B2 | 7/2010 | Becker et al. |
| 7,799,411 B2 | 9/2010 | Ostendorf et al. |
| 7,807,022 B2 | 10/2010 | Hermans et al. |
| 7,811,665 B2 | 10/2010 | Manifold et al. |
| 7,851,667 B2 | 12/2010 | Becker et al. |
| 7,869,964 B2 | 1/2011 | Rosati et al. |
| 7,894,625 B2 | 2/2011 | Tompkins, IV et al. |
| 7,914,649 B2 | 3/2011 | Ostendorf et al. |
| 7,922,705 B2 | 4/2011 | Ampulski |
| 7,939,168 B2 | 5/2011 | Manifold et al. |
| 7,960,020 B2 | 6/2011 | Manifold et al. |
| 7,967,950 B2 | 6/2011 | Horenziak et al. |
| 8,025,966 B2 | 6/2011 | Manifold et al. |
| 7,989,058 B2 | 8/2011 | Manifold et al. |
| 8,034,463 B2 | 10/2011 | Leimbach et al. |
| RE42,968 E | 11/2011 | Sheehan et al. |
| 8,135,170 B2 | 3/2012 | Tompkins, IV et al. |
| 8,163,130 B2 | 4/2012 | Polat et al. |
| 8,178,196 B2 | 5/2012 | Manifold et al. |
| 8,192,836 B2 | 6/2012 | Manifold et al. |
| 8,202,605 B2 | 6/2012 | Ostendorf et al. |
| 8,211,271 B2 | 7/2012 | Polat et al. |

(56) References Cited

U.S. PATENT DOCUMENTS

| | | | |
|---|---|---|---|
| 8,282,783 B2 | 10/2012 | Phan et al. |
| 8,287,693 B2 | 10/2012 | Phan et al. |
| 8,298,376 B2 | 10/2012 | Polat et al. |
| 8,313,617 B2 | 11/2012 | Polat et al. |
| 8,657,997 B2 | 2/2014 | Polat et al. |
| 2002/0168518 A1 | 11/2002 | Bond et al. |
| 2003/0077444 A1 | 4/2003 | Bond et al. |
| 2003/0092343 A1 | 5/2003 | Bond et al. |
| 2003/0138597 A1 | 7/2003 | Ruthven et al. |
| 2003/0168912 A1 | 9/2003 | Wodrich et al. |
| 2003/0181115 A1 | 9/2003 | Nagasuna et al. |
| 2004/0023003 A1 | 2/2004 | Basler et al. |
| 2004/0099387 A1 | 5/2004 | Vinson et al. |
| 2004/0112783 A1 | 6/2004 | Mukai et al. |
| 2004/0154767 A1 | 8/2004 | Trokhan et al. |
| 2004/0154768 A1 | 8/2004 | Trokhan et al. |
| 2004/0154769 A1 | 8/2004 | Lorenz et al. |
| 2004/0157524 A1 | 8/2004 | Polat et al. |
| 2004/0162536 A1 | 8/2004 | Becker et al. |
| 2004/0167486 A1 | 8/2004 | Busam et al. |
| 2004/0170813 A1* | 9/2004 | Digiacomantonio ........................ A61F 13/511 428/195.1 |
| 2004/0192136 A1 | 9/2004 | Gus-ky et al. |
| 2004/0258887 A1 | 12/2004 | Maciag et al. |
| 2004/0261639 A1 | 12/2004 | Vaughn et al. |
| 2005/0026529 A1 | 2/2005 | Bond |
| 2005/0034828 A1 | 2/2005 | Graff et al. |
| 2005/0045293 A1 | 3/2005 | Hermans et al. |
| 2005/0067126 A1 | 3/2005 | Horenziak et al. |
| 2005/0079785 A1 | 4/2005 | Bond et al. |
| 2005/0178513 A1 | 8/2005 | Russell et al. |
| 2005/0201965 A1 | 9/2005 | Kuhlman et al. |
| 2006/0137840 A1 | 6/2006 | Burazin et al. |
| 2006/0286343 A1 | 12/2006 | Curro et al. |
| 2007/0156108 A1 | 7/2007 | Becker et al. |
| 2007/0167928 A1 | 7/2007 | Becker et al. |
| 2007/0179464 A1 | 8/2007 | Becker et al. |
| 2007/0232178 A1 | 10/2007 | Polat et al. |
| 2007/0254550 A1 | 11/2007 | Hamed et al. |
| 2007/0256802 A1 | 11/2007 | Sheehan et al. |
| 2008/0041543 A1 | 2/2008 | Dyer et al. |
| 2008/0125735 A1 | 5/2008 | Busam et al. |
| 2008/0260996 A1 | 10/2008 | Heilman et al. |
| 2008/0312622 A1 | 12/2008 | Hundorf et al. |
| 2009/0043273 A1 | 2/2009 | Carlucci et al. |
| 2009/0099793 A1 | 4/2009 | Rosati et al. |
| 2009/0110998 A1 | 4/2009 | Miyachi et al. |
| 2009/0118689 A1 | 5/2009 | Lawson et al. |
| 2009/0220741 A1 | 9/2009 | Manifold et al. |
| 2009/0220769 A1 | 9/2009 | Manifold et al. |
| 2009/0287174 A1 | 11/2009 | Carlucci et al. |
| 2010/0036342 A1 | 2/2010 | Carlucci et al. |
| 2010/0051166 A1 | 3/2010 | Hundorf |
| 2010/0228210 A1 | 9/2010 | Busam et al. |
| 2010/0228211 A1 | 9/2010 | Becker et al. |
| 2010/0239946 A1 | 9/2010 | Miyachi et al. |
| 2010/0249740 A1 | 9/2010 | Miyamoto et al. |
| 2010/0294446 A1 | 11/2010 | Manifold et al. |
| 2011/0027563 A1 | 2/2011 | Manifold et al. |
| 2011/0114277 A1 | 5/2011 | Spitzer et al. |
| 2011/0137624 A1 | 6/2011 | Weisman |
| 2011/0139389 A1 | 6/2011 | Phan et al. |
| 2011/0139390 A1 | 6/2011 | Phan et al. |
| 2011/0183132 A1 | 7/2011 | Manifold et al. |
| 2011/0189435 A1 | 8/2011 | Manifold et al. |
| 2011/0189436 A1 | 8/2011 | Manifold et al. |
| 2011/0189442 A1 | 8/2011 | Manifold et al. |
| 2011/0189443 A1 | 8/2011 | Manifold et al. |
| 2011/0189451 A1 | 8/2011 | Manifold et al. |
| 2011/0206913 A1 | 8/2011 | Manifold et al. |
| 2011/0207837 A1* | 8/2011 | Luckert .................... C08J 11/08 521/40 |
| 2011/0212299 A1 | 9/2011 | Nyangiro et al. |
| 2011/0253329 A1 | 10/2011 | Manifold et al. |
| 2011/0305884 A1 | 12/2011 | Manifold et al. |
| 2012/0107568 A1 | 5/2012 | Manifold et al. |
| 2012/0226250 A1 | 9/2012 | Sato et al. |
| 2013/0167305 A1 | 7/2013 | Weisman |
| 2013/0226120 A1 | 8/2013 | Van De Maele |
| 2014/0053994 A1 | 2/2014 | Manifold et al. |
| 2014/0163511 A1 | 6/2014 | Roe et al. |
| 2015/0080826 A1 | 3/2015 | Ehrnsperger et al. |
| 2015/0250660 A1 | 9/2015 | Tally et al. |
| 2016/0136009 A1 | 5/2016 | Weisman et al. |
| 2016/0136011 A1 | 5/2016 | Weisman et al. |
| 2016/0136013 A1 | 5/2016 | Weisman et al. |

FOREIGN PATENT DOCUMENTS

| | | |
|---|---|---|
| EP | 1 505 207 A2 | 2/2005 |
| EP | 0 677 612 B2 | 6/2006 |
| EP | 1447066 | 10/2008 |
| EP | 2740449 | 11/2014 |
| GB | 2319539 A | 5/1998 |
| GB | 2510665 | 8/2014 |
| WO | WO 96/33310 A1 | 10/1996 |
| WO | WO 97/17494 A1 | 5/1997 |
| WO | WO-9718783 | 5/1997 |
| WO | WO 98/44194 A1 | 10/1998 |
| WO | WO 95/11652 | 3/1999 |
| WO | WO 2005/021868 A1 | 3/2005 |
| WO | WO 2005/068720 A1 | 7/2005 |
| WO | WO 2005/080683 A2 | 9/2005 |
| WO | WO 2006/060814 A2 | 6/2006 |
| WO | WO 2007/001576 A1 | 1/2007 |
| WO | WO 2007/070124 A1 | 6/2007 |
| WO | WO 2012/052172 | 4/2012 |

OTHER PUBLICATIONS

International Search Report and Written Opinion, PCT/US2017/021470, dated May 12, 2017.

El-Hosseiny, et al., "Effect of Fiber Length and Coarseness of the Burst Strength of Paper", TAPPI Journal, vol. 82: No. 1 (Jan. 1999), pp. 202-203.

Smook, Gary A., Second Edition Handbook for Pulp & Paper Technologists, 1992, Angus Wilde Publications, Chapter 13, pp. 194-208.

* cited by examiner

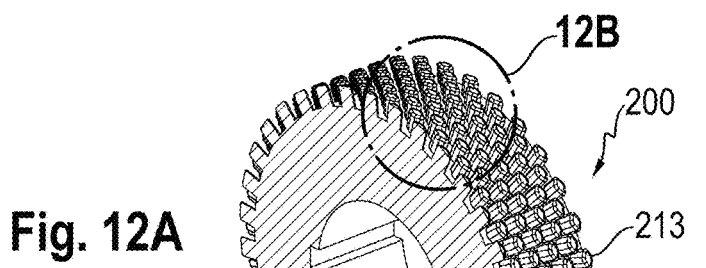
Fig. 12A
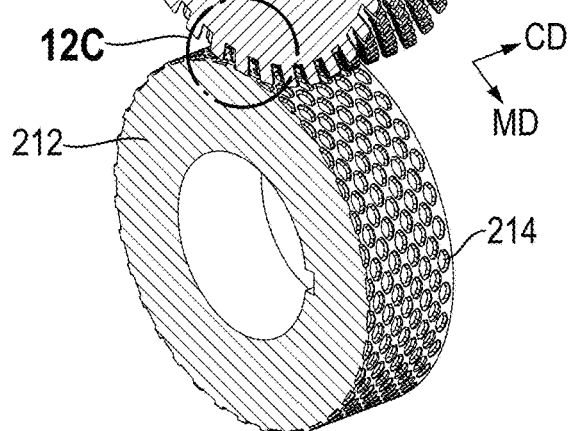
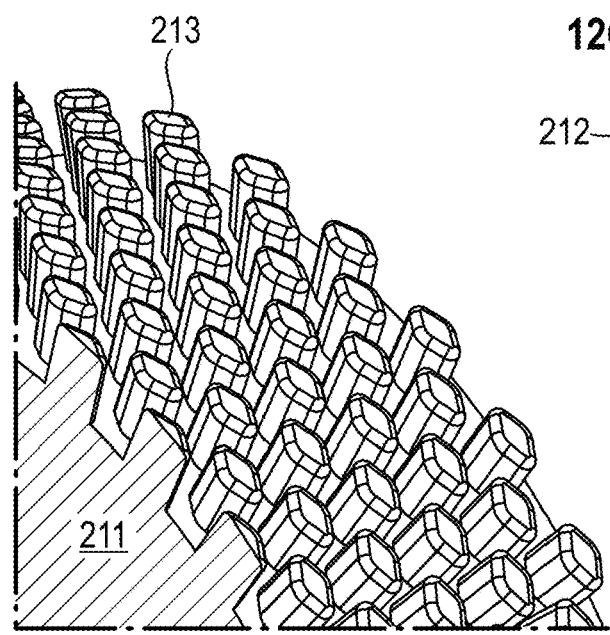
Fig. 12B
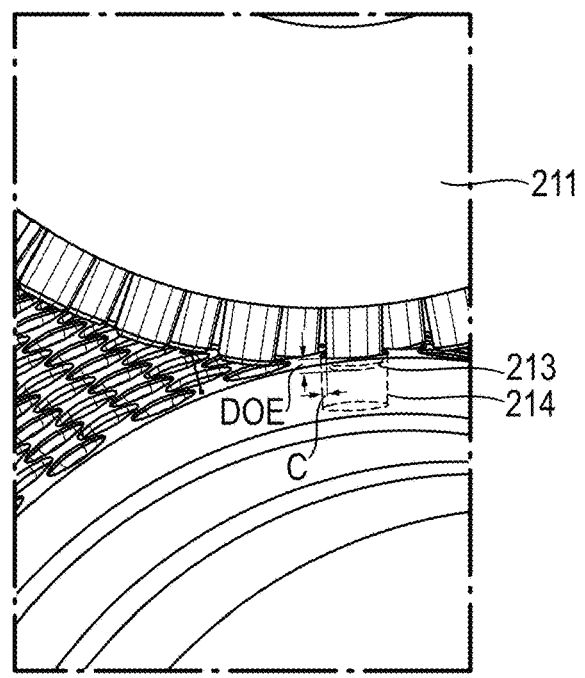
Fig. 12C

THREE-DIMENSIONAL SUBSTRATE COMPRISING A TISSUE LAYER

CROSS REFERENCE TO RELATED APPLICATION

This application claims the benefit, under 35 U.S.C. § 119(e), to U.S. Provisional Patent Application No. 62/306,676 filed on Mar. 11, 2016, which is hereby incorporated by reference herein in its entirety.

FIELD OF THE INVENTION

The invention provides a three-dimensional substrate comprising at least two layers wherein the first layer may be a liquid permeable topsheet or an acquisition layer and wherein the second layer is a tissue layer. The three-dimensional substrate may be used in an article for personal hygiene such as a baby diaper, a training pant, a feminine hygiene sanitary napkin or an adult incontinence product.

BACKGROUND OF THE INVENTION

An absorbent article typically comprises a topsheet, a backsheet, and an absorbent core disposed between the topsheet and the backsheet. The absorbent article can further include an acquisition layer and optionally a distribution layer. The acquisition layer is able to receive the liquid bodily exudates from the topsheet in order to temporary store them. Then, the optional distribution layer can receive the liquid bodily exudates from the acquisition layer and distribute and transfer them to the absorbent core. Such absorbent articles exhibit satisfactory fluid handling properties.

Three-dimensional structures have been developed; see for example U.S. Patent application U.S. Pat. Publ. No, 2014/0121625 A1.

There still remains a need to further improve the fluid-handling properties of these three dimensional structure when subjected to several gushes of bodily exudates.

There is a need to develop an absorbent article comprising a three-dimensional substrate which can provide improved fluid handling properties such as reduced rewet onto the wearer-facing surface of the absorbent article and better liquid acquisition, while at the same time providing sufficient physical and perceptional comfort of the absorbent article.

Moreover, at the end of the manufacturing process, the absorbent article comprising a three-dimensional substrate are typically folded and packaged as is known in the art. The absorbent articles may be packed under relatively high compression so as to reduce the size of the packages, while still providing an adequate amount of absorbent articles per package. However, the compression applied on the absorbent articles may have negative effects on the three-dimensional substrate. Indeed, the three-dimensional substrate may be deformed or collapsed which may affect the fluid handling properties of the three-dimensional substrate and the perceptional comfort of the absorbent article.

Thus, there is also a need to provide a three-dimensional substrate that presents an improved caliper recovery after compression.

SUMMARY OF THE INVENTION

A three-dimensional substrate is provided and has a first surface, a second surface, land areas and comprises three-dimensional protrusions extending outward from the second surface of the three-dimensional substrate. The three-dimensional protrusions are surrounded by the land areas. The three-dimensional substrate is a laminate comprising at least two layers in a face to face relationship. The second layer is a tissue layer facing outward from the second surface of the three-dimensional substrate. The tissue layer comprises at least 80% pulp fibers by weight of the tissue layer.

The first layer may be a liquid permeable topsheet or an acquisition layer.

The three-dimensional substrate may comprise at least two layers comprising fibers. The three-dimensional protrusions may be formed from the fibers of at least two layers of the three-dimensional substrate. A majority of the three-dimensional protrusions may comprise a base forming an opening, an opposed distal portion, and one or more side walls between the bases and the distal portions of the majority of the three-dimensional protrusions. The base, distal portion and the one or more side walls may be formed by fibers such that the majority of the three-dimensional protrusions may have only one opening at the base.

The tissue layer may be a wet-laid. The tissue layer comprises pulp fibers. The other layers comprised in the three-dimensional substrate may be nonwoven webs. Therefore, the density of the tissue layer may be higher than the density of the other layer. The tissue layer may reinforce the structure of the three-dimensional protrusions, in particular along the side walls of the three-dimensional protrusions. Hence, the majority of the three-dimensional protrusion can be better preserved after being subjected to any inherent compressive forces. The three-dimensional substrate can thereby have an improved caliper recovery after compression.

The three-dimensional substrate may comprise holes formed in the tissue layer at the opposed distal portions of the majority of the three-dimensional protrusions.

At least 50% to 100% of the three-dimensional protrusions may have holes formed in the tissue layer at the distal portions of the three-dimensional protrusions; or at least 70% to 100% of the three-dimensional protrusions may have holes formed in the tissue layer at the distal portions of the three-dimensional protrusions.

During the formation of the three-dimensional substrate and due to the characteristics of the tissue layer, when the three-dimensional topology is imparted to the structure, the tissue layer has a tendency to break at the opposed distal portion of the three-dimensional protrusions forming holes at the distal portions of the three-dimensional protrusions. When the three-dimensional substrate is incorporated into an absorbent article, the plurality of holes in the tissue layer of the three-dimensional substrate allows the absorbent article to have a better absorption of liquid, such as liquid bodily exudates, at the opposed distal portion of the three-dimensional protrusions.

The tissue layer can provide a natural hydrophilic material (i.e. the pulp fibers) for capillary connectivity between the layers of the three-dimensional substrate. As a second layer, the tissue layer improves the dewatering of the first layer that may be in contact with liquid bodily exudates. Therefore, when the three-dimensional substrate is incorporated into an absorbent article, this three-dimensional substrate can reduce the contact of the liquid bodily exudates with the skin of the wearer.

The three-dimensional substrate may consist of two layers wherein the first layer of the three-dimensional substrate is the liquid permeable topsheet to form a topsheet/tissue layer laminate.

Alternatively, the three-dimensional substrate may consist of two layers wherein the first layer of the three-dimensional substrate is the acquisition layer to form an acquisition layer/tissue layer laminate.

In a further alternative, the three-dimensional substrate may consist of three layers wherein the first layer is the acquisition layer and the third layer is the liquid permeable topsheet, to form topsheet/acquisition layer/tissue layer laminate. The layers of the laminate are in a face to face relationship. In such structures, the first layer is in between the third layer and the second layer.

The first layer and the third layer may be nonwoven web.

The layers in closed contact to each other form a heterogeneous structure where the side walls of a majority of the three-dimensional protrusions comprise at least two layers and the opposed distal portions of a majority of the three-dimensional protrusions comprise at least one layer. Indeed, the three-dimensional substrate may comprise holes formed in the tissue layer at the opposed distal portions of the majority of the three-dimensional protrusions.

Thus, the opacity contrast between the side walls and the opposed distal portions of a majority of three-dimensional protrusions is improved. Thereby, the three-dimensional protrusions may be more visible. Moreover, the tissue layer increases the opacity of the three-dimensional substrate especially in the land area between each three-dimensional protrusion allowing the three-dimensional substrate to better mask the liquid bodily exudates.

The invention also relates to an absorbent article for personal hygiene comprising a longitudinal axis, a transversal axis perpendicular to the longitudinal axis, a three-dimensional substrate described herein, an absorbent core and a backsheet. The absorbent core may be located between the three-dimensional substrate and the backsheet.

BRIEF DESCRIPTION OF THE DRAWINGS

FIG. 12A is a perspective view of an apparatus comprising a first and second forming member for forming the three-dimensional substrate of the invention.

FIG. 12 B is a perspective view of a portion of the first forming member of the apparatus shown in FIG. 12A.

FIG. 12C is a perspective view of the apparatus shown in FIG. 12A, showing the first forming member intermeshing with the second forming member.

DETAILED DESCRIPTION OF THE INVENTION

Definition of Terms

Figure 1:
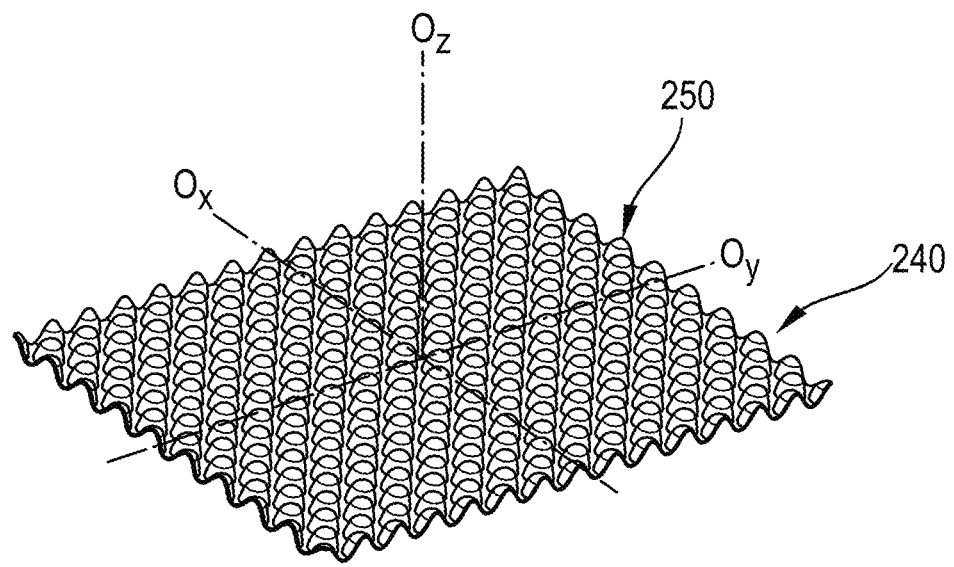
FIG. 1 is a top perspective view for the portion of a three-dimensional substrate in accordance with the present invention.

The term "three-dimensional substrate" as used herein refers to a substrate having a base and comprising three-dimensional protrusions. According to the invention, the three-dimensional substrate is a laminate comprising at least two layers wherein the second layer is a tissue layer.

The term "laminate" as herein refers to an intimate combination of at least two layers disposed in a face to face relationship forming a three-dimensional substrate. The second layer is a tissue layer. The first layer may be a liquid permeable topsheet or an acquisition layer.

The term "topsheet/tissue layer laminate" as used herein refers to an intimate combination of a topsheet as a first layer with the tissue layer as a second layer, disposed in face to face relationship. When the three-dimensional substrate described herein is incorporated into an absorbent article, the topsheet is facing towards the body of the wearer. The tissue layer is facing towards the backsheet. The topsheet with the tissue layer can have undergone a simultaneous and joint mechanical deformation while they are combined with each other. The topsheet/tissue layer laminate comprises deformations forming three-dimensional protrusions. The topsheet/tissue layer laminate may be formed by nesting together the topsheet and the tissue layer wherein the three-dimensional protrusions of the topsheet coincide with and fit together with the three-dimensional protrusions of the tissue layer.

The term "acquisition layer/tissue layer laminate" as used herein refers to an intimate combination of an acquisition layer as a first layer with the tissue layer as a second layer, disposed in face to face relationship. When the three-dimensional substrate described herein is incorporated into an absorbent article, the acquisition layer is facing towards the body of the wearer. The tissue layer is facing towards the backsheet. The acquisition layer with the tissue layer can have undergone a simultaneous and joint mechanical deformation while they are combined with each other. The acquisition layer/tissue layer laminate comprises deformations forming three-dimensional protrusions. The acquisition layer/tissue layer laminate may be formed by nesting together the acquisition layer and the tissue layer, wherein the three-dimensional protrusions of the acquisition layer coincide with and fit together with the three-dimensional protrusions of the tissue layer, as shown in FIG. 12A.

The term "topsheet/acquisition layer/tissue layer laminate" as used herein refers to an intimate combination of a topsheet as a third layer with an acquisition layer as a first layer and a tissue layer as a second layer, disposed in a face to face relationship. When the three-dimensional substrate described herein is incorporated into an absorbent article, the topsheet is facing towards the body of the wearer. The acquisition layer is disposed between the topsheet and the tissue layer. The tissue layer is facing towards the backsheet. The topsheet, the acquisition layer and the tissue layer can have undergone a simultaneous and joint mechanical deformation while the topsheet, the acquisition layer and the tissue layer are combined with each other. The topsheet/acquisition layer/tissue layer laminate comprises deformations forming three-dimensional protrusions. In the topsheet/acquisition layer/tissue layer laminate, the topsheet, the acquisition layer and the tissue layer may be in an intimate contact with each other.

The term "extensible" as used herein refers to a material, which, upon application of a force, is capable of undergoing an apparent elongation of equal to or greater than at least 100% of its original length in the machine and/or cross-machine directions at or before reaching the breaking force if subjected to the following test:

The MD and CD tensile properties are measured using a method using WSP 110.4 (05) Part B, with a 50 mm sample width, 60 mm gauge length, and 60 mm/min rate of extension.

It may be desirable that a material is capable of undergoing an apparent elongation of equal to or greater than at least 100% or 110% or 120% or 130% up to 200% in the machine and/or cross-machine directions at or before reaching the breaking force according to the Test Method as set out above.

If a material is capable of undergoing an apparent elongation of less than 100% of its original length if subjected to the above described test, it is "non-extensible" as used herein.

The terms "holes", as used herein, refer to apertures formed in the tissue layer at the opposed distal portions of the majority of the three-dimensional protrusions during the formation of the three-dimensional substrate.

The term "mechanically deforming and combining" as used herein means that the at least two layers comprised in the three-dimensional substrate are put in a face to face relationship and can be simultaneously mechanically deformed between a first and second roll and intimately combined at the same time. The mechanical deformation of the layers depends on the process, the required apparatus but also on the properties of the layers, i.e. apparent elongation of the fibers, fiber mobility, ability to deform and stretch in the area where the three-dimensional protrusions of the laminate are formed, ability to undergo plastic deformation which sets after existing the first and second roll, or springing partially back due to elastic recovery.

The mechanical deformation may comprise engaging at least two layers together wherein the second layer is a tissue layer between a first and second forming member such that a plurality of deformations comprising three-dimensional protrusions are obtained. Alternatively, the mechanical deformation may comprise engaging at least two layers together wherein the second layer is a tissue layer between a first and second intermeshing rolls such that a plurality of deformations comprising three-dimensional protrusions are obtained.

The term "machine direction" or "MD" as used herein means the path that material, such as a web, follows through a manufacturing process.

The term "cross-machine direction" or "CD" as used herein means the path that is perpendicular to the machine direction in the plane of the web.

The term "wet-laid" as used herein is a process step in papermaking. In the wet-laid process, pulp fibers (wood or non-wood) are first mixed with chemicals and water to obtain a uniform dispersion called slurry at very high dilutions of 0.01 percent weight to 0.5 percent weight of the fibers. The slurry is then deposited on a moving foraminous member (or wire screen) where the excess water is drained off, leaving the fibers randomly laid in a uniform substrate, which is then bonded and finished as required.

The term "pulp" as used herein refers to refers to natural fibers which typically are wood pulp fibers. Applicable wood pulps comprise chemical pulps, such as Kraft, sulfite, and sulfate pulp, as well as mechanical pulps comprising, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers may be blended, or alternatively, may be deposited in layers to provide a stratified web. The term "substrate" as used herein refers to an individual, self-sustaining, integral web that may comprise one or more layers.

The term "fibrous substrate" as used herein refers to an individual, self-sustaining, integral web comprising pulp fibers. The fibrous substrate may comprise two or more stratified non-self-sustaining hardwood and/or softwood portions.

The term "dry-laid fiber" as used herein means fibers which have been provided in a fluid medium which is gaseous (air).

The term "web" as used herein means a material capable of being wound into a roll. Webs may be nonwovens.

The term "papermaking belt" as used herein refers to a structural element that is used as a support for the fiber or filaments that may be deposited thereon during a process of making a fibrous substrate, and as a forming unit to form a desired microscopical geometry of a fibrous substrate. The papermaking belt may comprise any element that has the ability to impart a three-dimensional pattern to the fibrous substrate being produced thereon, and includes, without limitation, a stationary plate, a belt, a cylinder/roll, a woven fabric, and a band.

The term "substantially continuous" regions as used herein refers to an area within which one can connect any two points by an uninterrupted line running entirely within that area throughout the line's length. That is, the substantially continuous region has a substantial "continuity" in all directions parallel to the first plane and is terminated only at edges of that region. The term "substantially," in conjunction with continuous, is intended to indicate that while an absolute continuity is desired, minor deviations from the absolute continuity may be tolerable as long as those deviations do not appreciably affect the performance of the fibrous substrates (or a papermaking belt) as designed and intended.

The term "substantially semi-continuous" regions as used herein refer to an area which has "continuity" in all, but at least one, directions parallel to the first plane, and in which area one cannot connect any two points by an uninterrupted line running entirely within that area throughout the line's length. The semi-continuous framework may have continuity only in one direction parallel to the first plane. By analogy with the continuous region, described above, while an absolute continuity in all, but at least one, directions is desired, minor deviations from such a continuity may be tolerable as long as those deviations do not appreciably affect the performance of the fibrous substrate.

The term "discrete zones" as used herein refer to regions that are discontinuous and separated from other areas in all directions parallel to the first plane.

The term "a majority of the three-dimensional protrusions" as used herein means that more than 50%, or more than 60%, or more than 70%, or more than 80%, or more than 90%, but not more than 95% of the three-dimensional protrusions in the three-dimensional substrate of the absorbent article.

The term "absorbent article" as used herein refers to disposable products such as diapers, pants or feminine hygiene sanitary napkins and the like which are placed against or in proximity to the body of the wearer to absorb and contain the various liquid bodily exudates discharged from the body. Typically these absorbent articles comprise a topsheet, backsheet, an absorbent core and optionally an acquisition layer and/or distribution layer and other components, with the absorbent core normally placed between the backsheet and the acquisition system or topsheet. The absorbent article of the present invention may be a diaper or pant.

The term "diaper" as used herein refers to an absorbent article that is intended to be worn by a wearer about the lower torso to absorb and contain liquid bodily exudates discharged from the body. Diapers may be worn by infants (e.g. babies or toddlers) or adults. They may be provided with fastening elements.

General Description of the Three-Dimensional Substrate 240

Referring to FIG. 1, an example of a three-dimensional substrate 240 is disclosed.

Structure

According to FIG. 1, the three-dimensional substrate 240 has land areas 243 and comprises three-dimensional protrusions 250. The land areas 243 may be substantially flat areas. The three-dimensional substrate 240 may comprise a majority of three-dimensional protrusions 250 having a first Z-directional height (Oz on FIG. 1). The majority of the three-dimensional protrusions 250 protrudes from the land areas 243 of the three-dimensional substrate 250 forming a base and an opposed distal portion from the land areas. The opposed distal portion of the majority of three-dimensional protrusions 250 extends to a distal end which forms a top peak which is spaced away from the base of the majority of three-dimensional protrusions 250. The base of the majority of three-dimensional protrusions 250 can be defined as the perimeter, which for circular protrusions, is the circumference, where each protrusion of the majority of three-dimensional protrusions 250 starts to protrude outwardly from the land areas of the three-dimensional substrate 240.

Figure 2:
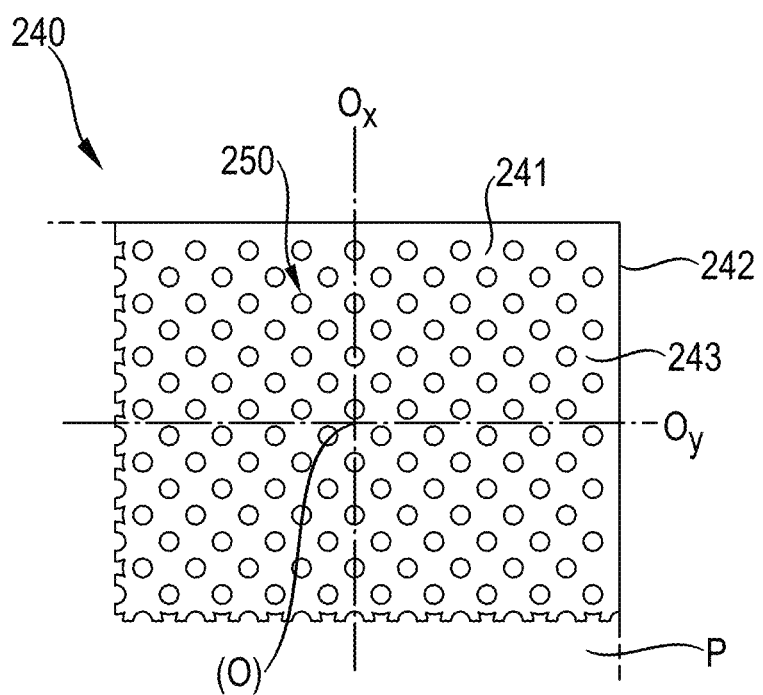
FIG. 2 is a top view of a portion of the three-dimensional substrate of FIG. 1.

Referring to FIG. 2, the three-dimensional substrate 240 forms a first surface 241 and a second surface 242. The majority of three-dimensional protrusions extend outward from the second surface 242 of the three-dimensional substrate 240. The majority of three-dimensional protrusions 250 are surrounded by a plurality of land areas 243 of the three-dimensional substrate 240. The plurality of land areas 243 of the three-dimensional substrate 240 may be located on the first surface 241 of the three-dimensional substrate 240. The majority of three-dimensional protrusions 250 of the three-dimensional substrate 240 may form a three-dimensional surface on the second surface 242 of the three-dimensional substrate 240.

The majority of three-dimensional protrusions 250 can be hollow. When viewing from the first surface 241 of the three-dimensional substrate 240, the majority of three-dimensional protrusions 250 may protrude from the land areas 243 of the three-dimensional substrate 240 in the same direction.

Alternatively, the three-dimensional protrusions 250 may protrude from the land area 243 of the three-dimensional substrate 240 in opposite direction.

The plurality of land areas 243 and the plurality of three-dimensional protrusions 250 together form the three-dimensional substrate 240.

The majority of the three-dimensional protrusions 250 may be generally dome-shaped.

Two or more adjacent three-dimensional protrusions 250 may be separated from each other by one or more land areas 243 in a direction generally perpendicular to the longitudinal axis or in a direction generally parallel to the longitudinal axis of the three-dimensional substrate 240.

The majority of the three-dimensional protrusions 250 extending outwardly from the first surface 241 of the three-dimensional substrate 240 may represent at least 20% or at least 30% or at least 40% or more than 50%, or more than 70%, or more than 80% but not more than 95% of the total area of the three-dimensional substrate 240.

The three-dimensional substrate 240 may be an absorbent three-dimensional substrate.

Characteristics of the Laminate

The three-dimensional substrate 240 is a laminate 245 comprising at least two layers in a face to face relationship. In other words, at least two layers are joined to form a laminate 245.

The three-dimensional substrate 240 comprises at least two layers in a face to face relationship wherein the first layer 246 may be a liquid permeable topsheet 24 or an acquisition layer 52 and wherein the second layer is the tissue layer 17 facing outward from the second surface 242 of the three-dimensional substrate 240. In other words, the tissue layer 17 forms the second surface 242 of the three-dimensional substrate 240.

The three-dimensional substrate 240 comprises at least a first layer 246 and a tissue layer 17 as a second layer.

The first layer 246 has a first surface 601 and a second surface 602.

The second layer, i.e. the tissue layer has a first surface 301 and a second surface 302.

The first layer 246 and the second layer, i.e. the tissue layer 17 are aligned in a face to face relationship such that the second surface 602 of the first layer 246 is in contact with the first surface 301 of the second layer, i.e. the tissue layer 17.

When the three-dimensional substrate described herein is incorporated into an absorbent article, the first layer 246 is facing towards the body of the wearer. The tissue layer 17 is facing towards the backsheet.

The first layer 246 and the second layer, i.e. the tissue layer 17 can be simultaneously mechanically deformed and combined together to provide the laminate 245 having three-dimensional protrusions 250. This means that both the first layer 246 and the tissue layer 17 can be mechanically deformed and combined together at the same time.

If the three-dimensional substrate 240 comprises two layers, the first layer 246 is a liquid permeable topsheet 24 or an acquisition layer 52, and the second layer is a tissue layer 17.

Alternatively, the first layer 246 of the three-dimensional substrate 240 may be the liquid permeable topsheet 24, and the second layer is the tissue layer 17. The three-dimensional substrate 240 may be a topsheet/tissue layer laminate.

The topsheet/tissue layer laminate may have a first surface and a second surface.

When the three-dimensional substrate 240 as topsheet/tissue layer laminate described herein is incorporated into an absorbent article, the first surface of the topsheet/tissue layer laminate may be in direct contact with the body of the wearer.

Alternatively, the first layer 246 of the three-dimensional substrate 240 may be the acquisition layer 52, and the second layer is the tissue layer 17. The three-dimensional substrate 240 may be an acquisition layer/tissue layer laminate.

The acquisition layer/tissue layer laminate may have a first surface and a second surface.

When the three-dimensional substrate 240 as an acquisition layer/tissue layer laminate described herein is incorporated into an absorbent article, the first surface of the acquisition layer/tissue layer laminate may be in direct contact with a flat topsheet or the first surface of the acquisition layer/tissue layer laminate may be in direct contact with the body of the wearer.

If the three-dimensional substrate 240 comprises three layers, the first layer 246 is an acquisition layer 52, the second layer is the tissue layer 17, and the third layer 247 is a liquid permeable topsheet 24. The three-dimensional substrate 240 may be a topsheet/acquisition layer/tissue layer laminate.

When the three-dimensional substrate described herein is incorporated into an absorbent article, the topsheet 24, i.e. the third layer 247 is facing towards the body of the wearer. The acquisition layer 52, i.e. the first layer 246 is disposed between the topsheet 24 and the tissue layer 17. The tissue layer 17, i.e. the second layer is facing towards the backsheet.

The third layer 247, i.e. liquid permeable topsheet 24 has a first surface 501 and a second surface 502.

The third layer 247, i.e. the topsheet 24, the first layer 246, i.e. the acquisition layer 52 and the second layer, i.e. the tissue layer 17 are aligned in a face to face relationship.

The second surface 502 of the third layer 247, i.e. the topsheet is in contact with the first surface 601 of the first layer 246, i.e. the acquisition layer.

The second surface 602 of the first layer 246, i.e. the acquisition layer is in contact with the first surface 301 of the second layer, i.e. the tissue layer 17.

The topsheet 24, the acquisition layer 52 and the tissue layer 17 can be simultaneously mechanically deformed and combined together to provide the topsheet/acquisition layer/tissue layer laminate 245 having three-dimensional protrusions 250.

Three-Dimensional Protrusions

Figure 3:
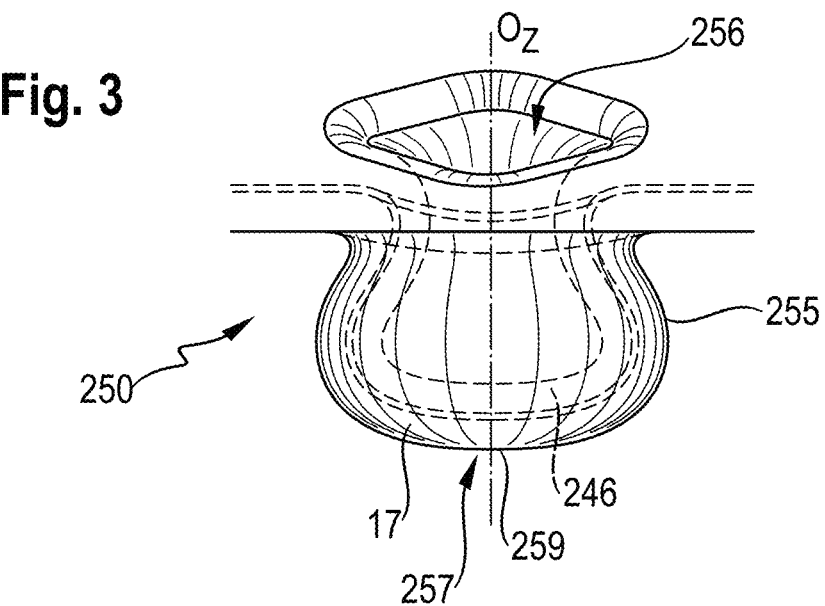
FIG. 3 is a perspective view of a three-dimensional protrusion of the three-dimensional substrate in accordance with the present invention.
Figure 4:
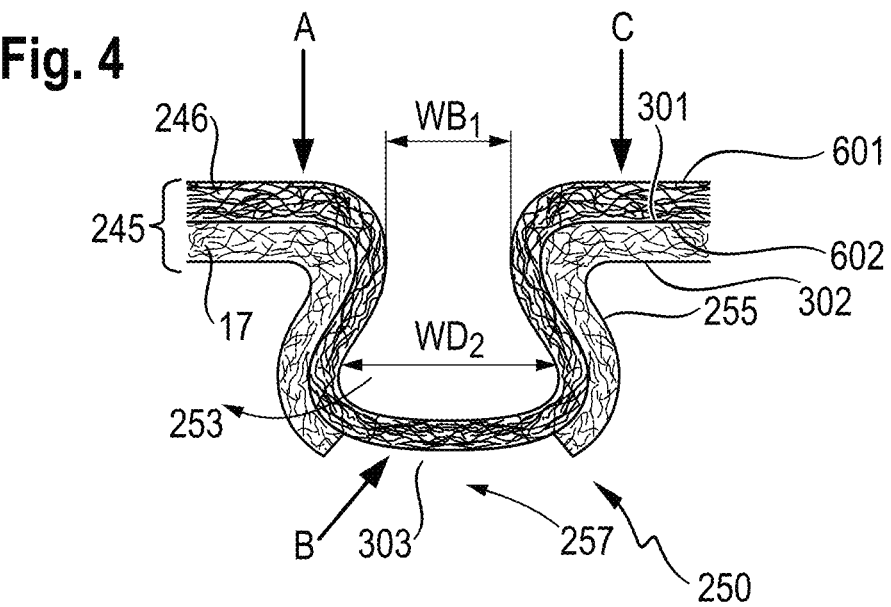
FIG. 4 is a schematic view of a three-dimensional protrusion of the three-dimensional substrate in accordance with the present invention.

Referring to FIG. 3 and FIG. 4, the three-dimensional protrusions 250 are, at least partly, formed from the fibers of at least two layers of the three-dimensional substrate 240.

The three-dimensional substrate 240 comprises at least a first layer 246 and a tissue layer 17 as a second layer. The first layer 246 may be a liquid permeable topsheet 24 or an acquisition layer 52.

As shown in FIG. 3, the majority of the three-dimensional protrusions 250 comprise a base 256 forming an opening and having a protrusion base width, an opposed distal portion 257, and one or more side walls 255 between the bases 256 and the opposed distal portions 257 of the majority of the three-dimensional protrusions. The base 256, distal portion 257 and the one or more side walls 255 are formed by fibers such that the majority of the three-dimensional protrusions 250 has only one opening at the base 256.

The majority of the three-dimensional protrusions 250 can be obtained by the mechanical process described in detail below.

The majority of the three-dimensional protrusions 250 may be more than 50% or more than 60% or more than 70% or more than 80% but not more than 95% of the three-dimensional protrusions 250 in the laminate 245.

The majority of the three-dimensional protrusions 250 of the laminate 245 may be provided throughout the complete surface of the laminate 245 or may only be provided in a portion of the surface of the laminate 245.

The three-dimensional protrusions 250 of the laminate 245 may be provided in an area of at least 30×40 mm of the surface of the laminate 245.

At least 10 three dimensional protrusions may be comprised by an area of at least 30×40 mm of the surface of the laminate 245.

An area of 10 cm$^2$ of the laminate 245 may comprise from 5 to 100 three-dimensional protrusions 250, from 10 to 50 three-dimensional protrusions 250 or from 20 to 40 three-dimensional protrusions 250.

In the area where the three-dimensional protrusions 250 of the laminate 245 are provided, the three-dimensional protrusions 250 may be uniformly distributed.

As shown in FIG. 4, the majority of the three-dimensional protrusion 250 may be made from engaging the first layer 246 with the tissue layer 17 such as the first layer 246 and the tissue layer 17 coincide with and fit together. Hence, as shown in FIG. 4, the first layer 246 and the tissue layer 17 are nested together.

The first layer 246 may comprise a plurality of fibers. The tissue layer 17 may comprise a plurality of fibers. The plurality of fibers composing the sidewalls 255 of the three-dimensional protrusion 250 may surround the side walls 255 of the three-dimensional protrusions 250. This means that there are multiple fibers which extend (e.g., in the z-direction) from the base 256 of the protrusions 250 to the distal end 257 of the protrusions, and contribute to form a portion of the side walls 255 of a three-dimensional protrusion 250, and these fibers are located substantially or completely around the perimeter of the protrusion 250.

The first layer 246 may be extensible, i.e. the fibers composing the first layer 246 may elongate.

Generally, the extensibility of the material composing the first layer 246 can be selected according to the desired sizes of the three-dimensional protrusions 250. If relatively large three-dimensional protrusions 250 are desired, materials with a relatively higher extensibility will be chosen.

For instance, the first layer 246 may be capable of undergoing an apparent elongation of equal to or greater than at least 100% or 110% or 120% or 130% up to 200% in the machine and/or cross-machine directions at or before reaching the breaking force according to the Test Method as set out in the Definition part. In some cases, it might be desired to have the majority of the three-dimensional protrusions 250 which are larger either in the machine or cross-machine direction.

Generally, the tissue layer 17 is inextensible.

If the three-dimensional substrate 240 comprises three layers, the topsheet, i.e. the third layer 247 and the acquisition layer, i.e. the first layer 246 may be extensible, i.e. the fibers composing the first layer 246 and the fibers composing the third layer 247 may elongate.

The majority of the three-dimensional protrusions 250 of the laminate 245 may at least be present in the first layer 246 and in the tissue layer 17, in the area where the first layer 246 overlaps the tissue layer 17 in the laminate 245.

As shown in FIG. 4, the majority of the three-dimensional protrusions 250 comprises an inside void volume 253 which is the portion of the three-dimensional protrusion which does not comprise any fibers or very little fibers. The void volumes 253 of the laminate 245 can improve the breathability of the laminate 245.

The majority of the three-dimensional protrusions 250 provide void volume to receive the liquid bodily exudates. When the three-dimensional substrate described herein is incorporated into an absorbent article, the three-dimensional substrate 240 may be in close contact with underlying layers such as a distribution layer. The underlying layers may be made of unconsolidated dry-laid fibers of a dry-laid fibrous structure or a wet-laid fibrous structure. The void volumes 253 of the laminate 245 can allow feces to be absorbed and acquired within them. In that case, the present invention is suitable to absorb feces of relatively low viscosity.

The majority of the three-dimensional protrusion 250 may be defined by a protrusion base width $WB_1$ of the base 256 forming an opening which is measured from two side walls of the inner portion at the base 256. The majority of the three-dimensional protrusion 250 may be defined by a width $WD_2$ of the inside void volume 253 which is the maximum interior width measured between two side walls of the inner three-dimensional protrusion or which is the maximum diameter of the side wall of the inner three-dimensional protrusion when the distal portion has a substantially circular shape. The maximum interior width $WD_2$ of the void area 253 at the opposed distal portion may be greater than the protrusion base width $WB_1$ of the base 256 of the three-dimensional protrusion 250. The protrusion base width $WB_1$ of the base 256 of the majority of the three-dimensional protrusion 250 may range from 0.5 mm to 15 mm or from 0.5 mm to 10 mm or from 0.5 mm to 5 mm or from 0.5 mm to 3 mm. Measurements of the dimensions of the protrusion base width $WB_1$ of the base 256 and the width $WD_2$ of the distal portion 257 can be made on a photomicrograph. When the size of the protrusion base width $WB_1$ of the base 256 is specified herein, it will be appreciated that if the openings are not of uniform width in a particular direction, the protrusion base width, $WB_1$, is measured at the widest portion. Measurements of the protrusion base width $WB_1$ of the base 256 or the maximum interior width $WD_2$ of the inside void area 253 at the distal portion 257 can be made on a photomicrograph at 20× magnification.

As the plurality of fiber composing the majority of the three-dimensional protrusions 250 may be present in the one or more side walls 255 of the majority of the three-dimensional protrusions 250, the majority of the three-dimensional protrusions may not collapse on one side and close off the opening at the base 256 when compressive forces are applied on the laminate 245. The opening at the base 256 may be maintained and may create a ring of increased opacity around the opening at the base 256 when the three-dimensional protrusion 250 has been compressed. Hence, the majority of the three-dimensional protrusion 250 can be preserved and remain visible to the consumer when viewing the three-dimensional substrate 240 from the first layer 246. The large distal portion 257 prevents the three-dimensional protrusion 250 from flopping over and pushing back into the original land areas 243 of the laminate 245.

Without wishing to be bound to any particular theory, the wide base 256, combined with the lack of a pivot point, causes the three-dimensional protrusions 250 to collapse in a controlled manner. Thus, the majority of the three-dimensional protrusions 250 are free of a hinge structure that would otherwise permit them to fold to the side when compressed.

Generally, the majority of the three-dimensional protrusions 250 may be configured to collapse in a controlled manner such that each base 256 forming an opening remains open, and the protrusion base width of each base 256 forming an opening is greater than 0.5 mm after compression.

It may be desirable for at least one of the three-dimensional protrusions 250 in the laminate 245 to collapse in a controlled manner described below under the 7 kPa load when tested in accordance with the Accelerated Compression Method in the Test Methods section below.

Alternatively, at least some, or in other cases, a majority of the three-dimensional protrusions 250 may collapse in the controlled manner described herein.

Alternatively, substantially all of the three-dimensional protrusions 250 may collapse in the controlled manner described herein. The ability of the three-dimensional protrusions 250 to collapse may also be measured under a load of 35 kPa, 4 kPa or 1 kPa. The 1 kPa, 4 kPa, 7 kPa and 35 kPa loads simulate manufacturing and compression packaging conditions. Wear conditions can range from 2 kPa or less up to 7 kPa.

In some forms, the ratio of the circumference length of the three-dimensional protrusions 250 to the length of the opening at the base 256 is less than 4:1.

To measure the circumference length of the three-dimensional protrusions 250, the three-dimensional substrate 240 comprising the three-dimensional protrusions is arranged so that the viewing direction is co-linear with the longitudinal axis (MD) of the three-dimensional protrusions. If necessary, a cross-section of the three-dimensional protrusions 250 can be obtained by cutting the three-dimensional protrusions perpendicular to the longitudinal axis using sharp scissors or a razor blade, taking care in preserving the overall geometry of the three-dimensional protrusions while cutting it.

As shown in FIG. 4, the circumference length of the three-dimensional protrusions 250 are measured and recorded by starting the measurement at a first origination point A, proceeding along the side walls 255 of the three-dimensional protrusions to the distal portion 257 of the three-dimensional protrusions 250 at a second point B (along the median path of the fibers) and terminating the measurement at the third origination point C. The length of the opening at the base 256 is measured and recorded parallel to the plane of the three-dimensional substrate 240 between the first origination point A and the third origination point C. The circumference length of the three-dimensional protrusions 250 are measured where the three-dimensional protrusions are not under any pressure or strain.

As shown in FIG. 4, the three-dimensional substrate 240 comprises holes 303 formed in the tissue layer 17 at the opposed distal portions 257 of the majority of the three-dimensional protrusions 250. In other words, the laminate 245 comprises holes 303 formed in the tissue layer 17 at the opposed distal portions 257 of the majority of the three-dimensional protrusions 250.

Generally, the tissue layer 17 is inextensible. During the formation of the three-dimensional substrate 240, the tissue layer may rupture and form holes 303, i.e. the fibers composing the tissue layer may be less extensible and/or less mobile than the fibers composing the first layer. In such case, the holes 303 may be formed by locally rupturing the tissue layer 17 by the process described in detail below.

The first layer 246 does not comprise holes at the opposed distal portions 257 of the three-dimensional protrusions 250.

If the three-dimensional substrate comprises three layers, the first layer and/or the third layer do not comprise holes at the opposed distal portions 257 of the three-dimensional protrusions 250.

When the three-dimensional substrate described herein is incorporated into an absorbent article, at the opposed distal portions 257 of the three-dimensional protrusions 250, the first layer 246 can be brought in direct contact with the underlying layer leading to a faster flow of liquid from the first layer 246 (and from the third layer 247 if present) through the underlying layer to the absorbent core 28.

The tissue layer 17 being naturally hydrophilic can also help to dewater the first layer 246 of the laminate 245.

At least 50% to 100% of the three-dimensional protrusions 250 may have holes 303 formed in the tissue layer 17 at the opposed distal portions 257 of the three-dimensional protrusions 250, or at least 70% to 100% of the three-dimensional protrusions may have holes 303 formed in the tissue layer 17 at the opposed distal portions 257 of the three-dimensional protrusions 250, or at least 80% to 10% of the three-dimensional protrusions may have holes 303 formed in the tissue layer 17 at the opposed distal portions 257 of the three-dimensional protrusions 250, or at least 90% to 100% of the three-dimensional protrusions 250 may have holes 303 formed in the tissue layer 17 at the opposed distal portions 257 of the three-dimensional protrusions 250.

When the three-dimensional substrate described herein is incorporated into an absorbent article, the plurality of holes 303 in the tissue layer 17 of the three-dimensional substrate 240 allows the absorbent article to have a better absorption of liquid bodily exudates at the opposed distal portion 257 of the three-dimensional protrusions 250.

Moreover, the tissue layer 17 has a density that may be higher than the density of the first layer 246 or the density of the first layer 246 (and of the third layer 247, if present) comprised in the three-dimensional substrate 240. The tissue layer may reinforce the structure of the three-dimensional protrusions, in particular along the side walls 255 of the three-dimensional protrusions where there are no holes 303 in the tissue layer. Hence, the majority of the three-dimensional protrusion 250 can be preserved after being subjected to any inherent compressive forces. The three-dimensional substrate 240 can thereby have an improved caliper recovery after compression.

Thus, due to the higher density of the tissue layer 17 and the presence of holes 303, the absorption of liquid bodily exudates and the resiliency to compression forces can be improved.

Furthermore, the layers in closed contact to each other in the three-dimensional substrate 240 form a heterogeneous structure where the side walls 255 of a majority of the three-dimensional protrusions 250 comprise at least two layers and the opposed distal portions 257 of a majority of the three-dimensional protrusions 250 comprises at least one layer but no tissue layer due to the formation of holes 303.

Thus, the opacity contrast between the side walls 255 and the opposed distal portions 257 of a majority of three-dimensional protrusions 250 is improved. A majority of three-dimensional protrusions 250 may be more visible. Moreover, the tissue layer 17 increases the opacity of the three-dimensional substrate 240 in the land area 243 and in the side walls 255 of the three-dimensional protrusions 250 allowing the three-dimensional substrate 240 to better mask the liquid bodily exudates.

The three-dimensional substrates of the present invention may comprise one or more colors, dyes, inks, indicias, patterns, embossments, and/or graphics. The colors, dyes, inks, indicias, patterns, and/or graphics may aid the aesthetic appearance of the three-dimensional substrates.

The Tissue Layer

As mentioned above, the three-dimensional substrate 240 comprises at least two layers in a face to face relationship wherein the second layer is a tissue layer 17 facing outward from the second surface of the three-dimensional substrate 240.

Precursor Tissue Layer

Figure 5:
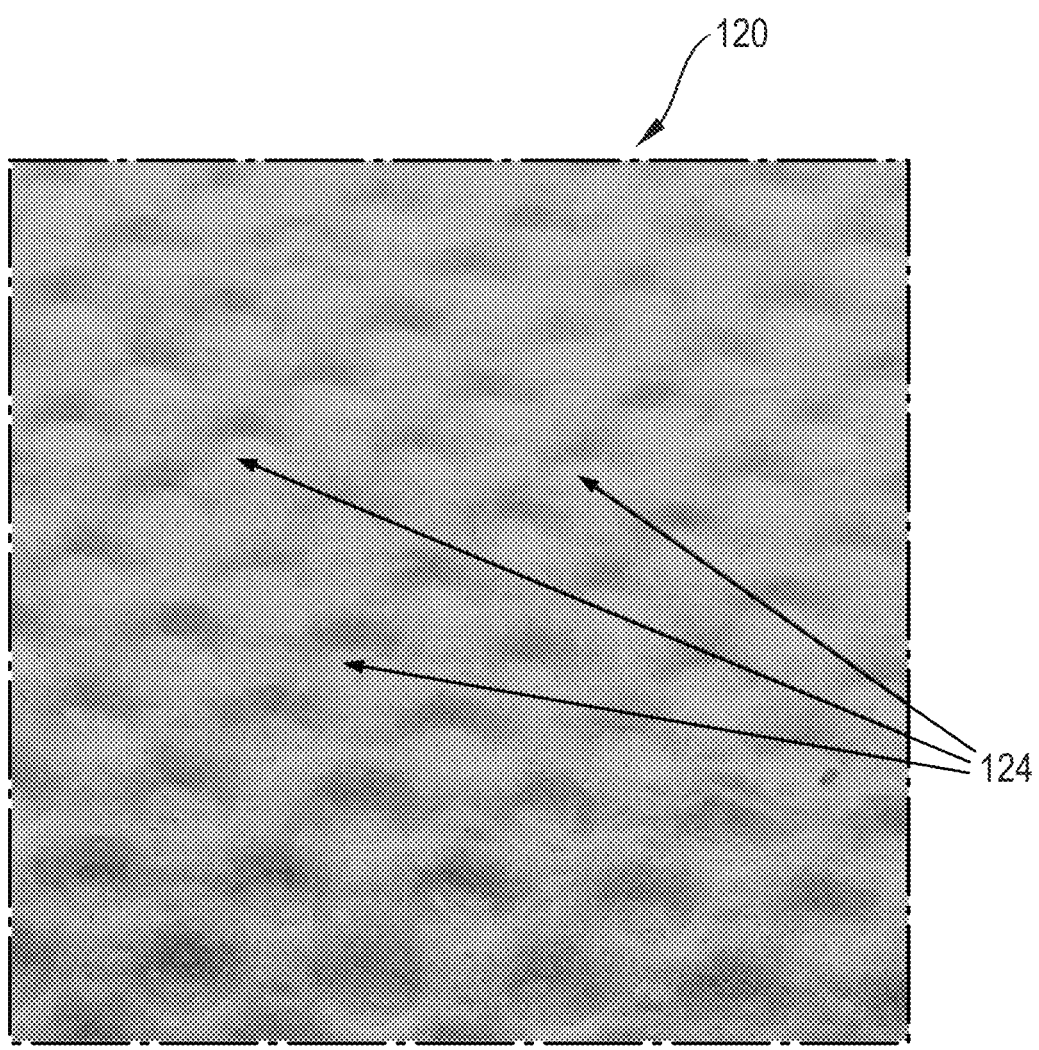
FIG. 5 is an enlarged photographic view of a precursor tissue layer in accordance with the present invention.

Referred to FIG. 5, the precursor tissue layer 120 is the ingoing material before being mechanically deformed into the tissue layer 17 of the three-dimensional substrate 240.

The precursor tissue layer 120 may be a three-dimensional fibrous before the three-dimensional protrusions are formed.

The tissue layer 17 may comprises at least 80%, or at least 90% pulp fibers by weight of the tissue layer 17.

The tissue layer 17 may comprise from 70% to 100%, or at least 80%, or at least 85%, or at least 90%, or at least 95%, or at least 99% pulp fibers by weight of the tissue layer 17.

Due to the high concentration of pulp fibers, the density of the tissue layer 17 may be higher than the density of the other layer comprised in the three-dimensional substrate 240. The tissue layer 17 may reinforce the structure of the three-dimensional protrusions, in particular along the side walls 255 of the three-dimensional protrusions 250. Hence, the majority of the three-dimensional protrusion 250 can be preserved after being subjected to any inherent compressive forces. The three-dimensional substrate 240 can thereby have an improved resiliency to the compression forces. The fluid handling properties of the three-dimensional substrate 240 is, in consequence, improved.

The precursor tissue layer 120 may be made of wet-laid fibers.

The precursor tissue layer 120 comprises pulp fibers. The precursor tissue layer 120 can provide a natural hydrophilic material for capillary connectivity between the first layer 246 of the laminate 245 and the underlying layers. Hence, the tissue layer 17 can help dewatering the first layer 246 of the three-dimensional substrate 240 by providing a capillary connectivity between the layers of three-dimensional substrate 240.

The wet-laid fibers may be produced by forming a predominantly aqueous slurry comprising 90% to 99.9% water or other suitable fluid or liquid. In one form, the non-aqueous component of the slurry used to make the wet-laid fibers may comprise from 1% to 95% or 5% to 80% of cellulosic fibers, such as *eucalyptus* fibers, by weight of the non-aqueous components of the slurry. In another form, the non-aqueous components may comprise from 8% to 60% of pulp fibers, such as *eucalyptus* fibers, by weight of the non-aqueous components of the slurry, or from 15% to 30% of pulp fibers, such as *eucalyptus* fibers, by weight of the non-aqueous component of the slurry. In some instances, the slurry may comprise 45% to 60% of Northern Softwood Kraft fibers with up to 20% Southern Softwood Kraft co-refined together, 25% to 35% unrefined *Eucalyptus* fibers and from 5% to 30% of either repulped product broke or thermo-mechanical pulp. Any other suitable pulp fibers and/or combinations thereof within the knowledge of those of skill in the art may also be used.

The precursor tissue layer 120 may comprise a mixture of at least two different materials. At least one of the materials may comprise a non-naturally occurring fiber, such as a polypropylene fiber or a polyolefin fiber, for example, and at least one other material, different from the first material, comprising a solid additive, such as another fiber and/or a particulate, for example.

Synthetic fibers useful herein may comprise any suitable material, such as, but not limited to polymers, those selected from the group consisting of polyesters, polypropylenes, polyethylenes, polyethers, polyamides, polyhydroxyalkanoates, polysaccharides, and combinations thereof. More specifically, the material of the polymer segment may be selected from the group consisting of poly(ethylene terephthalate), poly(butylene terephthalate), poly(1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer), polycaprolactone, poly(hydroxyl ether ester), poly(hydroxyl ether amide), polyesteramide, poly(lactic acid), polyhydroxybutyrate, and combinations thereof.

Further, the synthetic fibers may be a single component fibers (i.e., single synthetic material or a mixture to make up the entire fiber), multi-component fibers, such as bi-component fibers (i.e., the fiber is divided into regions, the regions including two or more different synthetic materials or mixtures thereof), and combinations thereof. Non-limiting examples of suitable bicomponent fibers are fibers made of copolymers of polyester (polyethylene terephthalate/isophtalate/polyester (polyethylene terephthalate) otherwise known as "CoPET/PET" fibers, which are commercially available from Fiber Innovation Technology, Inc., Johnson City, Tenn.

The pulp fibers may also comprise non-wood fibers. Non-wood fibers may comprise fibers made from polymers, specifically hydroxyl polymers. Non-limiting examples of suitable hydroxyl polymers include polyvinyl alcohol, starch, starch derivatives, chitosan, chitosan derivatives, cellulose derivatives, gums, arabinans, galactans, and combinations thereof. Additionally, other synthetic fibers such as rayon, polyethylene, and polypropylene fibers can be used within the scope of the present disclosure.

Non-wood pulp fibers may also comprise fibers that comprise processed residuals from agricultural crops such as wheat straw, wetland non-tree plants such as bulrush, aquatic plants such as water hyacinth, microalgae such as *Spirulina* and macroalgae seaweeds such as red or brown algae. Examples of non-wood natural materials include, but are not limited to, wheat straw, rice straw, flax, bamboo, cotton, jute, hemp, sisal, bagasse, hesperaloe, switchgrass, *miscanthus*, marine or fresh water algae/seaweeds, and combinations thereof.

To enhance permanent wet strength of one or more precursor tissue layer 120, cationic wet strength resins may be added to the papermaking furnish or to the embryonic web.

The precursor tissue layer 120 made of wet-laid fibers may comprise one or more cationic wet strength resins selected from the group consisting of a base activated epoxide polyamide epichlorohydrin resin, an urea-formaldehyde resin, a melamine formaldehyde resin, a polyamide-epichlorohydrin resin, a polyethyleneimine resin, a polyacrylamide resin, a dialdehyde starch and mixtures thereof.

The cationic wet strength resins may comprise cationic water soluble resins. These resins may improve wet strength in a fibrous substrate. This resin may improve either temporary or permanent wet strength to the fibrous substrate. KYMENE® resins obtainable from Hercules Inc., Wilmington, Del. may be used, including KYMENE® 736 which is a polyethyleneimine (PEI) wet strength polymer. It is believed that the PEI may improve wet strength by ionic bonding with the pulps carboxyl sites. KYMENE® 557LX is polyamide epichlorohydrin (PAE) wet strength polymer. It is believed that the PAE contains cationic sites that may lead to resin retention by forming an ionic bond with the carboxyl sites on the pulp. KYMENE® 450 is a base activated epoxide polyamide epichlorohydrin polymer. It is theorized that like 557LX the resin attaches itself ionically to the pulps' carboxyl sites via the epoxide groups of 557LX. KYMENE® 2064 is also a base activated epoxide polyamide epichlorohydrin polymer. It is theorized that KYMENE® 2064 may improve its wet strength by the same mechanism as KYMENE® 450. KYMENE® 2064 differs in that the polymer backbond contains more epoxide functional groups than does KYMENE® 450. Mixtures of the foregoing may be used. Other suitable types of such resins include urea-formaldehyde resins, melamine formaldehyde resins, polyamide-epichlorohydrin resins, polyethyleneimine resins, polyacrylamide resins, dialdehyde starches, and mixtures thereof.

The Structure of the Precursor Tissue Layer

Figure 6:
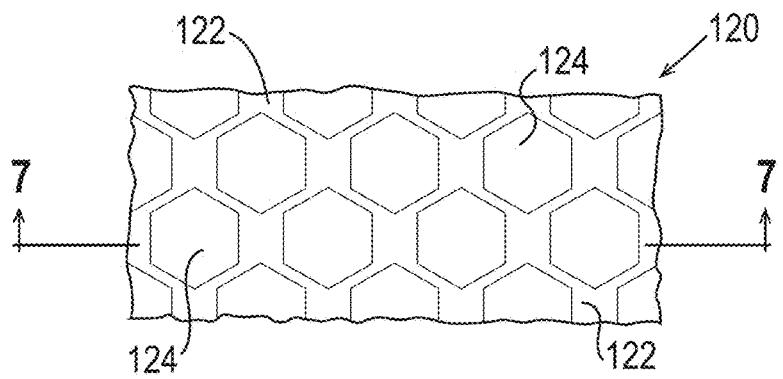
FIG. 6 is an example plan view of a precursor tissue layer of a tissue layer in accordance with the present disclosure.
Figure 7:
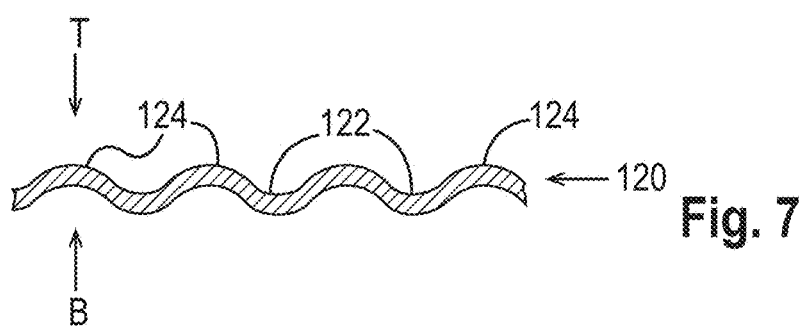
FIG. 7 is a cross-sectional view of a precursor tissue layer taken along line 7-7 of FIG. 6.

Referring to FIGS. 5, 6 and 7, a precursor tissue layer 120 is formed that has at least a first region which is a continuous network region 122 and a second region which is a plurality of discrete zones 124.

The precursor tissue layer 120 is subsequently incorporated into the three-dimensional structure of the three-dimensional substrate 240. The three-dimensional protrusions 250 of the three-dimensional substrate 240 do not correspond to the discrete zones 124 of the precursor tissue layer 120.

The precursor tissue layer 120 comprises a continuous network region 122 and a plurality of discrete zones 124 wherein the discrete zones 124 are dispersed throughout the continuous network region 122.

The continuous network region may not be completely planar but may comprise indentations (indented into the page, i.e. towards the other side of the fibrous web relative to the plurality of discrete zones 124).

Alternatively to being continuous or substantially continuous, the network region may be substantially semicontinuous.

FIG. 6 illustrates a plan view a portion of the precursor tissue layer 120 where the continuous network region 122 is illustrated as defining hexagons, although it is to be understood that other preselected patterns may also be used.

FIG. 7 is a cross-sectional view of precursor tissue layer 120 taken along line 7-7 of FIG. 6. As can be seen from the example of FIG. 7, the continuous network region 122 is essentially monoplanar. The plurality of discrete zones 124 are dispersed throughout the entire continuous network region 122 and essentially each discrete zone 124 is encircled by the continuous network region 122. The shape of the discrete zones 124 may be defined by the continuous network region 122. As shown in FIG. 7, the discrete zones 124, extend from (protrude from) the plane formed by continuous network region 122 toward an imaginary observer looking in the direction of arrow T of FIG. 7. When viewed by an imaginary observer looking in the direction indicated by arrow B of FIG. 7, the plurality of discrete zones 124 may comprise accurately shaped voids which appear to be cavities or dimples.

Figure 8:
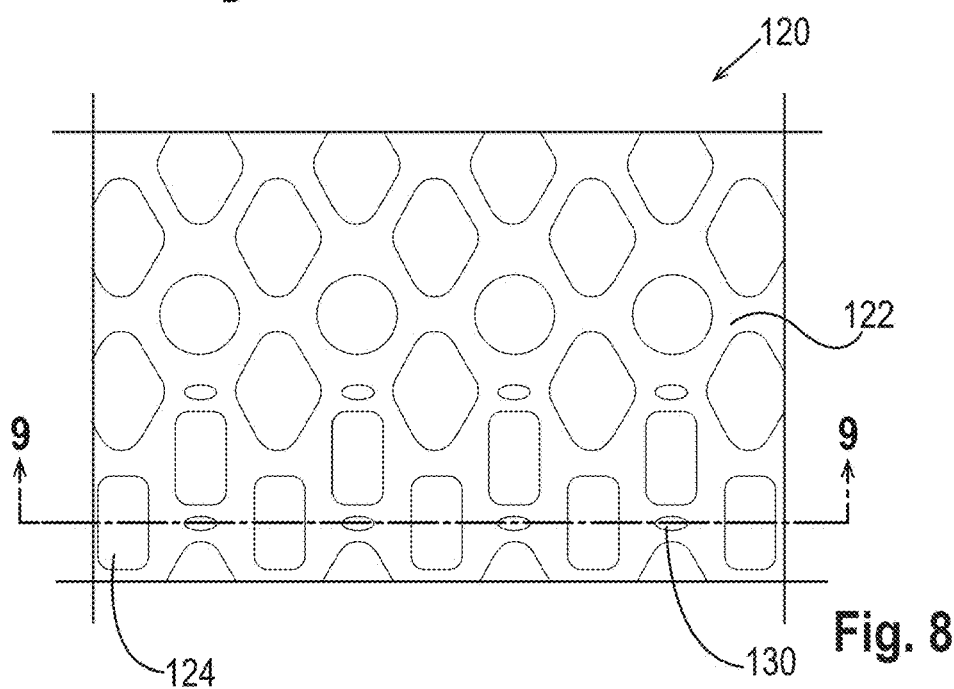
FIG. 8 is another example plan view of the precursor tissue layer of the tissue layer in accordance with the present disclosure.
Figure 9:
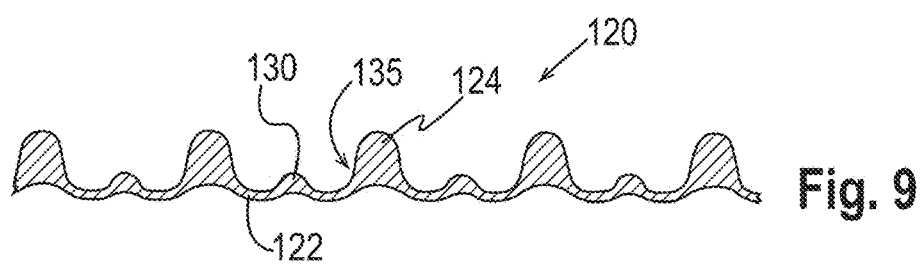
FIG. 9 is a cross-sectional view of the precursor tissue layer taken along line 9-9 of FIG. 8.

The plurality of discrete zones 124 may not all have the same height (i.e. the same caliper). This is exemplary shown in FIGS. 8 and 9, where a first plurality of discrete zones 124 has a first caliper, and second plurality of discrete zones 130 has a second caliper. In the fibrous web shown in FIGS. 8 and 9, the second caliper is smaller than the first caliper. In addition, the fibrous web may have third, fourth, fifth and further discrete zones which differ from each other (and differ from the first and second caliper).

In one instance, three-dimensional fibrous web may be creped or uncreped. The continuous network region may have a first basis weight and the plurality of discrete zones may have a second, different basis weight. The continuous network region may have a first caliper or elevation and the plurality of discrete zones may have a second caliper or elevation. The first and second calipers or elevations may be different.

The common property of the precursor tissue layer such as, for example, the basis weight, caliper, elevation, opacity, average density, wet burst strength, total dry tensile strength, tensile energy absorption, geometric mean modulus, and/or geometric mean peak elongation may be disclosed in the patent application PCT/US2015/059363, filed on the 11 Jun. 2015, by The Procter & Gamble Company.

It will be recognized that any suitable number of layers of precursor tissue layer 120 may be combined to form a tissue layer 17 or a portion thereof, as is described in further detail herein.

The precursor tissue layer 120 of the present invention can be made on a papermaking belt. U.S. Pat. Appl. Publ. No. 2013/0209749A1 (Myangiro) describes a method for making a precursor tissue layer 120 of the present invention utilizing a papermaking belt, or "molding member".

A web of a precursor tissue layer 120 of the tissue layer 17 may be made through the use of a patterned papermaking belt 300 for forming three-dimensionally structured wet-laid webs as described in U.S. Pat. No. 4,637,859, issued Jan. 20, 1987, to Trokhan.

Figure 10:
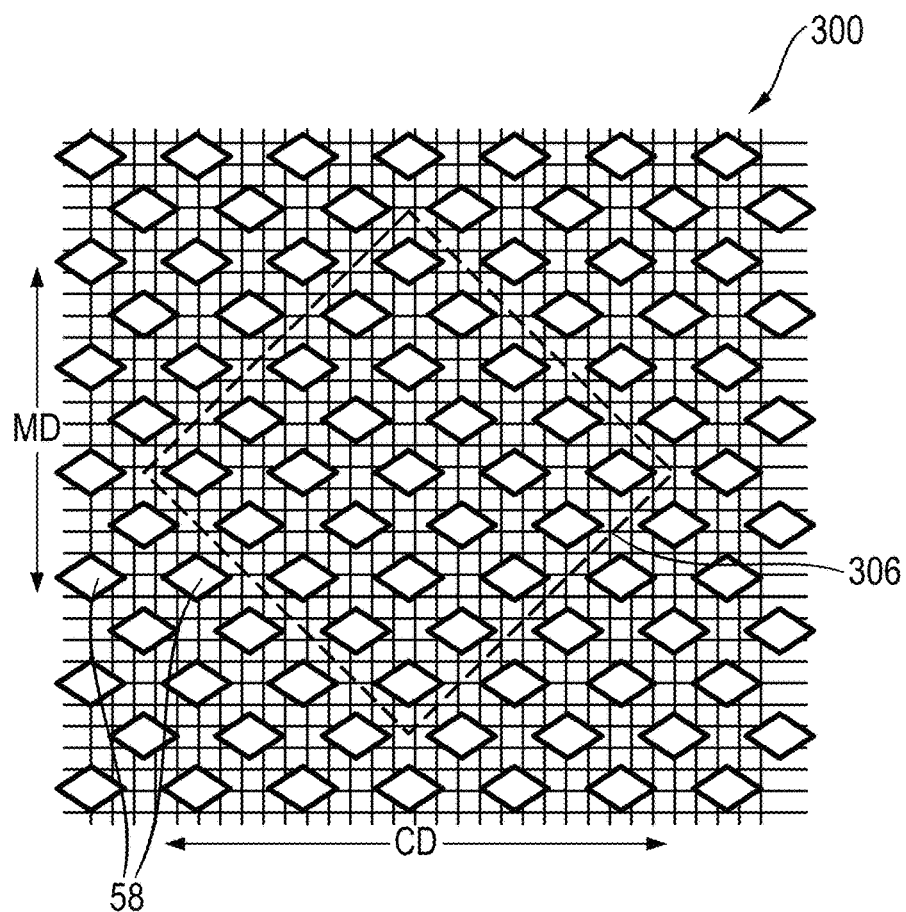
FIG. 10 is a plan view of a portion of a molding member of a papermaking belt for making the precursor tissue layer of the present invention.

Referring again to FIG. 10, the precursor tissue layer 120 may be formed using the patterned papermaking belt 300 having the plurality of raised resin portions 58, each raised resin portion 58 forming a corresponding (high density) discrete zone 124 in the fibrous substrate. The areas of the papermaking belt 300 that do not have the raised resin portions 58 form the continuous network region 122 (low density) in the fibrous substrate. In the alternative, the raised resin portions may form a continuous network on the papermaking belt 300, which would correspondingly form a high density continuous network region in the fibrous substrate, while the areas on the papermaking belt not having the raised resin portions would form the low density discrete elements in the fibrous substrate (not illustrated). The raised resin portion 58 may have any suitable shape such as round, ovate, square, rectangular, trapezoidal, or polygonal shape. One unit 306 (shown by dashed line) of one example of a pattern of the papermaking belt 300 is illustrated.

Figure 11:
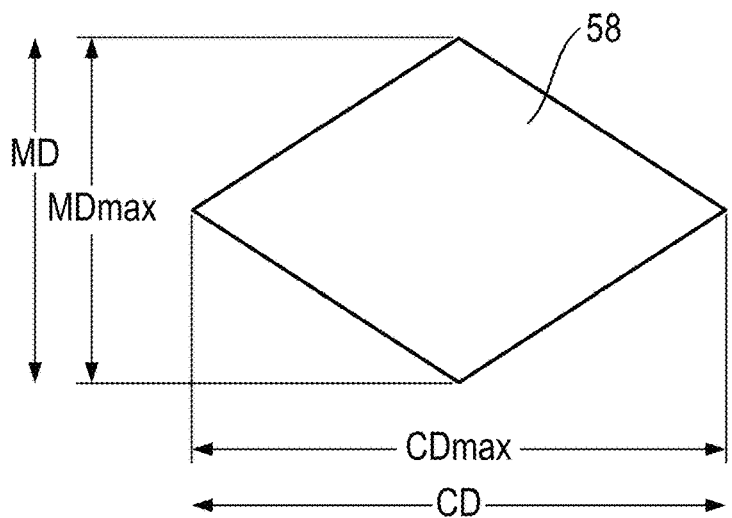
FIG. 11 is a plan view of an example of a raised portion of a molding member for making a precursor tissue layer of the present invention.

Referring again to FIG. 11, a top view of an individual raised resin portion 58 that forms an individual discrete element is illustrated separate from the papermaking belt 300 for clarity. The raised resin portion 58 may have any suitable shape, such as a generally elongated shape having a major axis, CDmax, and a minor axis, MDmax. One papermaking belt 300 may have more than one shape of raised resin portions. In general, the dimensions of the discrete zone 124 of the precursor tissue layer 120 are determined by the dimensions of the corresponding raised portions 58 that they are formed on. That is, the precursor tissue layer 120 is generally formed over the three-dimensional structure of the papermaking belt 300, so that in one sense the fibers are formed over, or molded to, the raised resin portions 58. If the raised resin portions form a continuous network, then the continuous network in the precursor tissue layer 120 may be formed on the raised resin portions, while the discrete elements will be formed in deflection conduits intermediate portions of the raised resin portions.

The ratio of the length of axis, CDmax, to the length of axis, MDmax, may be greater than or equal to one or less than 1. Stated another way, the axis, CDmax, may be longer than, shorter than, or may have the same length as the axis, MDmax. In one form, the ratio of the length of the axis, CDmax, to the length of the axis, MDmax, may be in the range of 1 to 3 or in the range of 1 to 4 or more.

In one form, the CDmax of one raised resin portion 58 may be between 1.50 mm to 3.50 mm, 1.55 mm to 2.00 mm, or 1.53 mm and 2.29 mm, and the MDmax of one raised portion 58 may be between 0.80 mm to 2.00 mm, 1.00 mm to 1.70 mm, or 1.01 mm to 1.53 mm, specifically reciting al 0.01 mm increments within the above-specified ranges and all ranges formed therein or thereby.

Some example shapes of the discrete zones (formed by the raised portions or raised resin portions) may comprise circles, ovals, squares, rectangles, ellipses, and polygons having any suitable number of sides. There is no requirement that the discrete zones be regular polygons or that the sides of the discrete zones 124 be straight. Instead, the discrete zones may comprise curved sides, stepped sides, or other multi-level sides.

First Layer

As explained above, the three-dimensional substrate 240 comprises at least a first layer 246 and a tissue layer 17 as a second layer. The first layer 246 may be a liquid permeable topsheet 24 or an acquisition layer 52.

The first layer 246 of three-dimensional substrate 240 of the present invention can be made of any suitable nonwoven materials ("precursor materials"). In some cases, the first layer may also be free of cellulose materials. The precursor materials for the first layer 246 may have suitable properties in order to be deformed. The suitable properties of the precursor materials may include: apparent elongation of the fibers, fiber mobility, ability to deform and stretch in the area where the three-dimensional protrusions 250 of the laminate 245 are formed. Hence, the precursor materials are capable of undergoing mechanical deformation to ensure that the three-dimensional protrusion 250 will not tend to recover or return to the prior configuration of a flat topsheet 24 or a flat acquisition layer 52.

Liquid Permeable Topsheet

Several examples of nonwoven materials suitable for use as a liquid permeable topsheet 24 for the laminate 245 may include, but are not limited to: spunbonded nonwovens; carded nonwovens; and nonwovens with relatively specific properties to be able to be readily deformed.

One suitable nonwoven material as a liquid permeable topsheet 24 for the laminate 245 may be an extensible polypropylene/polyethylene spunbonded nonwoven. One suitable nonwoven material as a liquid permeable topsheet 24 for the laminate 245 may be a spunbonded nonwoven comprising polypropylene and polyethylene. The fibers may comprise a blend of polypropylene and polyethylene. Alternatively, the fibers may comprise bi-component fibers, such as a sheath-core fiber with polyethylene on the sheath and polypropylene in the core of the fiber.

The liquid permeable topsheet 24 of the laminate 245 may have a basis weight from 8 to 40 gsm or from 8 to 30 gsm or from 8 to 20 gsm.

Acquisition Layer

Suitable nonwoven materials for the acquisition layer 52 of the laminate 245 may include, but are not limited to: spunbonded nonwovens, through-air bonded ("TAB") carded high loft nonwoven materials, spunlace nonwovens, hydroentangled nonwovens, and resin bonded carded nonwoven materials.

Spunbonded PET may be denser than carded nonwovens, providing more uniformity and opacity. Since PET fibers are not very extensible, the nonwoven can be bonded such that at least some of the fibers can be separated easily from the bond sites to allow the fibers to pull out of the bond sites and rearrange when the material is strained. This type of bonding, e.g. pressure bonding can help increasing the level of mobility of the fibers. Indeed, the fibers tend to pull out from the bond sites under tension.

The acquisition layer exhibits a basis weight from 10 to 120 gsm or from 10 to 100 gsm or from 10 to 80 gsm.

The first layer 246 and the tissue layer 17 may be joined together prior or during the mechanical deformation. If desired an adhesive, chemical bonding, resin or powder bonding, or thermal bonding between the first layer 246 with the tissue layer 17 may be selectively utilized to bond certain regions or all of the first layer 246 and the tissue layer 17 together. In addition, the first layer 246 and the tissue layer 17 may be bonded during processing, for example, by carding the first layer 246 of onto the tissue layer 17 and thermal point bonding the combined layers.

Prior to any mechanical deformation, the first layer 246 may be attached to the tissue layer 17. For instance, the first layer 246 may be attached to the tissue layer 17 where the first layer 246 and the tissue layer 17 overlaps. The attachment of the first layer to the tissue layer 17 may include a uniform continuous layer of adhesive, a discontinuous patterned application of adhesive or an array of separate lines, spirals, or spots of adhesive. The basis weight of the adhesive in the laminate 245 may be from 0.5 to 30 gsm or from 1 to 10 gsm or from 2 to 5 gsm.

If the three-dimensional substrate comprises three layers, the first layer 246, i.e. the acquisition layer 52 may be attached to the second layer, i.e. the tissue layer 17 and to the third layer 247, i.e. the topsheet 24. The attachment of the acquisition layer between the topsheet and the tissue layer may include a uniform continuous layer of adhesive, a discontinuous patterned application of adhesive or an array of separate lines, spirals, or spots of adhesive.

Alternatively, the first layer 246, i.e. the acquisition layer 52 may be attached to the second layer, i.e. the tissue layer 17 but not to the third layer 247, i.e. the topsheet, or vice versa.

The Mechanical Deformations and the Resulting Three-Dimensional Protrusions

The first layer 246 and the tissue layer 17 may be engaged together between a first and second forming members (211, 212) and be simultaneously mechanically deformed and combined together to form the laminate 245, as exemplified in FIGS. 12A, 12B and 12C. The laminate 245 comprises thus deformations forming three-dimensional protrusions 250.

The first and second forming member (211, 212) may be drum-shaped, generally cylindrical as shown in FIGS. 12A, 12B and 12C, or plate-shaped.

The first forming member 211 of the apparatus 200 may have a surface comprising a plurality of discrete, spaced apart male forming elements 213 having a base that is joined to the first forming member 211, a top that is spaced away from the base, and sides that extend between the base and the top of the male forming elements 213. The male forming elements 213 may have a plan view periphery, and a height.

The top on the male forming elements 213 may have a rounded diamond shape, see for example FIG. 12B, with vertical sidewalls and a radiused or rounded edge at the transition between the top and the sidewalls of the male forming element 213.

The region between the top and the side walls of the male forming elements 213 may also be of any suitable configuration. This region between the top and the side walls of the male forming elements 213 can be in the form of a sharp edge in which case there is zero, or a minimal radius where the side walls and the top of the male forming elements meet. That is, the region between the top and the side walls of the male forming elements 213 may be substantially angular, sharp, non-radiused, or non-rounded. In other embodiments, the region between the top and the side walls of the male forming elements 213 can be radiused, or alternatively beveled. Suitable radiuses include, but are not limited to: zero (that is, the transition forms a sharp edge), 0.01 inch (about 0.25 mm), 0.02 inch (about 0.5 mm), 0.03 inch (about 0.76 mm), 0.04 inch (about 1 mm) (or any 0.01 inch increment above 0.01 inch), up to a fully rounded male forming elements 213.

The second forming member 212 may have a surface comprising a plurality of recesses 214 in the second forming member 212. The recesses 214 may be aligned and configured to receive the respective male forming elements 213 therein. Hence, each recess 214 of the second forming member 212 may be sufficiently large to be able to receive each respective male forming element 213 of the first forming member 211. The recesses 214 may have a similar shape as the male forming elements 213. The depth of the recesses 214 may be greater than the height of the male forming elements 213.

The first and second forming member 211, 212 may be further defined by a depth of engagement (DOE) which is a measure of the level of intermeshing of the first and second forming member (211, 212), as shown in FIG. 12C. The depth of engagement (DOE) may be measured from the tip of the male forming elements 213 to the outermost portion of the surface of the second forming member 212 which portions are not within a recess 214. The depth of engagement (DOE) may range from 1.5 mm to 5.0 mm or from 2.5 mm to 5.0 mm or from 3.0 mm to 4.0 mm.

The first and second forming member 211, 212 may be defined by a clearance between the first and second forming member 211, 212 as shown in FIG. 12C. The clearance is the distance between the side wall of the male forming element 213 and the side wall of the recess 214. The clearance may range from 0.1 mm to 2 mm or from 0.1 mm to 1.5 mm from 0.1 mm to 1 mm.

The first layer 246 and the tissue layer 17 may be therefore engaged together between the first and second forming members 211, 212 and be mechanically deformed and combined together to form the laminate 245. The laminate 245 comprises mechanical deformations forming three-dimensional protrusions 250.

The laminate 245 may be notionally divided into a first and second area. The first and/or second area of the laminate 245 may comprise the majority of the three-dimensional protrusions 250 having different shapes.

Viewed from a cross-sectional view, i.e. in a Z-direction, the majority of the three-dimensional protrusions 250 may have any suitable shapes which include, but are not limited to: cylindrical, bulbous-shaped, conical-shaped and mushroom shaped.

Viewed from above, the majority of the three-dimensional protrusions 250 may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions. The majority of the three-dimensional protrusions 250 may be non-circular.

The majority of the three-dimensional protrusions 250 may form, in conjunction, one or more graphics. Having graphics can support the caregiver's perception that the absorbent article is well able to absorb the liquid bodily exudates.

Also, the majority of the three-dimensional protrusions 250 may form, in conjunction, one or more graphics such as a logo, e.g. the Pampers Heart logo.

The majority of the three-dimensional protrusions 250 may have similar plan view dimensions in all directions, or the majority of the three-dimensional protrusions 250 may be longer in one dimension than another. The majority of the three-dimensional protrusions 250 may have different length and protrusion base width dimensions. The majority of the three-dimensional protrusions 250 may, thus, have a ratio of length to protrusion base width. The ratio of length to protrusion base width can range from 10:1 to 1:10.

Figure 22:
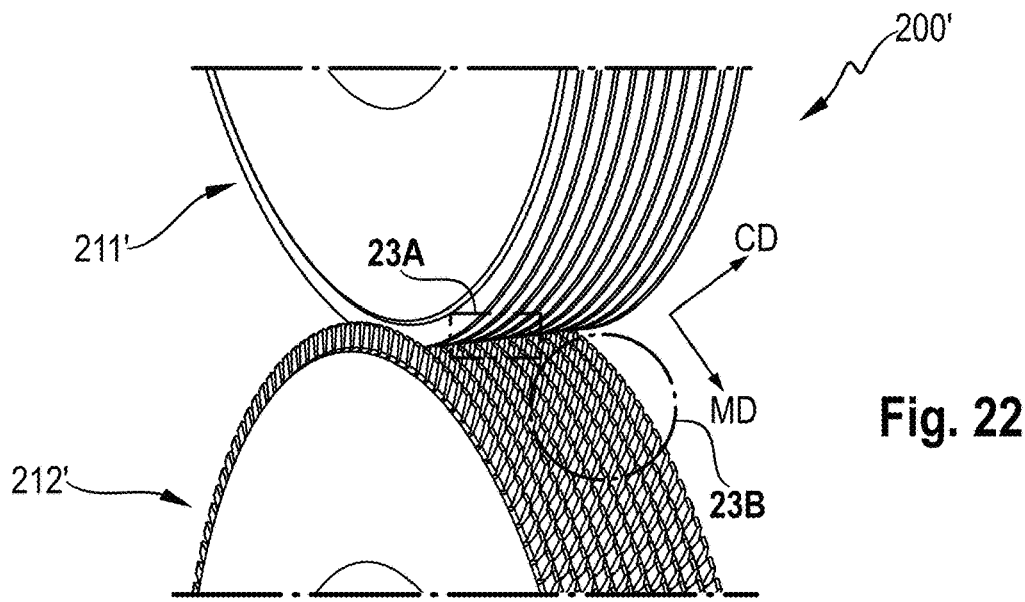
FIG. 22 is a perspective view of another apparatus comprising a first and second intermeshing roll for forming the laminate of the present invention.
Figure 23A:
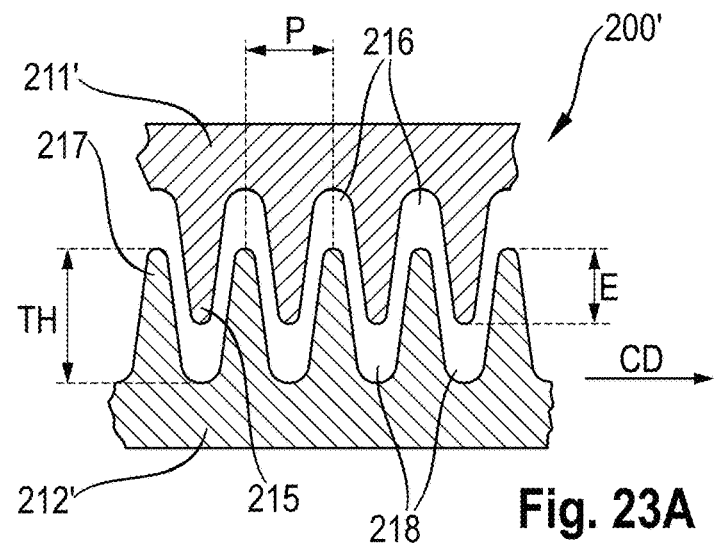
FIG. 23A is a cross-sectional depiction of a portion of the apparatus shown in FIG. 22.
Figure 23B:
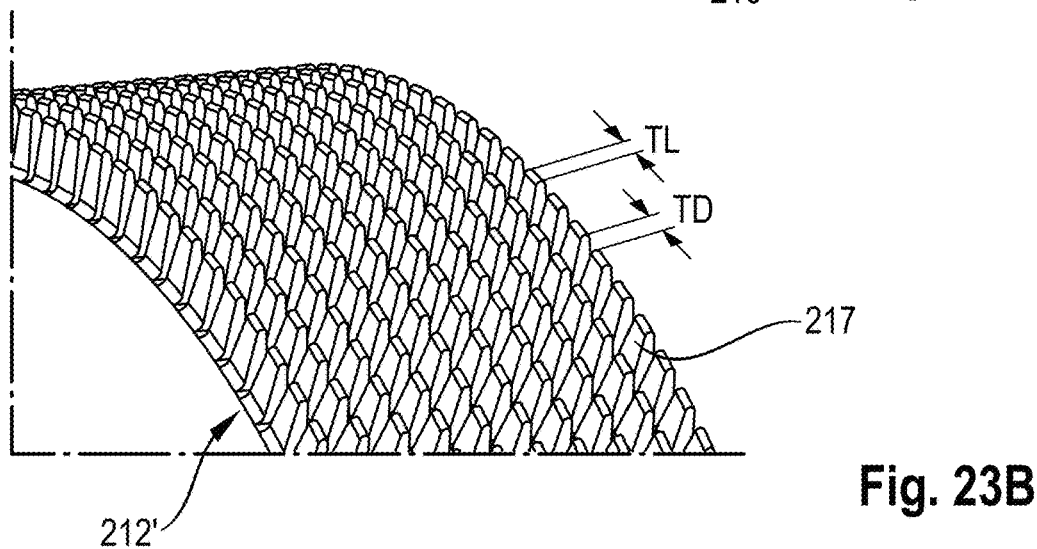
FIG. 23B is a perspective view of a portion of the second intermeshing roll of the apparatus shown in FIG. 22.

Another process may be used to mechanically deform and combine the first layer 146 and the tissue layer together in order to form the laminate 245. The step of the process related to mechanically deforming and combining the first layer 246 with the tissue layer 17 may comprise the following step of providing a first and second intermeshing roll 211', 212' as shown in FIGS. 22, 23A and 23B.

The first intermeshing roll 211' of an apparatus 200' may comprise a plurality of ridges 215 and corresponding grooves 216 which extend unbroken substantially about a circumference of the first intermeshing roll 211'.

The second intermeshing roll 212' may comprise a plurality of rows of circumferentially-extending ridges that have been modified to be rows of circumferentially-spaced teeth 217 and corresponding grooves 218, wherein the plurality of rows of circumferentially-spaced teeth 217 extend in spaced relationship about at least a portion of the second intermeshing roll 212'.

The first layer 246 and the tissue layer 17 may be intermeshed together between the first and second intermeshing rolls 211', 212' such that the ridges 215 of the first intermeshing roll 211' extend into the grooves 218 of the second intermeshing roll 212' and the teeth 217 of the second intermeshing roll 212' extend into the grooves 216 of the first intermeshing roll 211' to form the laminate 245. Hence, a plurality of deformations comprising three-dimensional protrusions 250 is obtained.

The first and second intermeshing roll 211'; 212' may be further defined by a tooth height TH, a pitch P and a depth of engagement E as shown in FIG. 23A. The tooth height TH may be measured from a surface of the second intermeshing roll 212 to a tip of a tooth 217. The tooth height TH may range from 0.5 mm to 10 mm or from 0.5 mm to 5 mm.

The pitch P may be defined as a tooth-to-tooth spacing which is measured from a tip of a first tooth to a tip of a second tooth of the second intermeshing roll 212'. The first and second tooth of the second intermeshing roll 212' may be located in the cross-machine direction. The pitch P may range from 1 mm to 10 mm or from 1 mm to 5 mm.

The depth of engagement E is a measure of how much the first and second intermeshing rolls 211', 212' are engaging with each other. The depth of engagement E may be measured from a tip of a ridge 215 to a tip of a tooth 217 which is located next to the ridge 215 in the cross-machine direction. The depth of engagement E may range from 0.5 mm to 10 mm or from 0.5 mm to 5 mm or from 1 to 4 mm.

Each tooth 217 of the second intermeshing roll 212' may be defined by a circumferential tooth length TL and a tooth distance TD, as shown in FIG. 23B. The circumferential tooth length TL may be measured from a leading edge to a trailing edge at a tooth tip. The tooth length TL may range from 0.5 mm to 10 mm or from 0.5 mm to 4 mm or from 1 mm to 4 mm.

Each tooth is separated from one another circumferentially by the tooth distance TD. The tooth distance TD may be measured from a leading edge of a first tooth to a trailing edge of a second tooth. The first and second teeth of the second intermeshing roll 212' may be on the same circumference in the machine direction. The tooth distance TD may range from 0.5 mm to 10 mm or from 0.5 mm to 5 mm or from 1 mm to 3 mm.

Other orientations of the teeth 217, grooves 216, 218 and ridges 215 may be possible, e.g. in CD direction versus MD direction.

While still providing the benefits mentioned, this process will produce differences in the structure of the three-dimensional protrusion 250 than that produced by the process shown in FIGS. 12A, 12B and 12C. The three-dimensional protrusion 250 produced by the intermeshing process shown in FIGS. 22, 23A and 23B may be a tunnel-shaped loop. Generally, a tunnel-shaped loop may comprise a base forming an opening and looped aligned fibers that create a tunnel shape with an opening at a leading edge and an opening at a trailing edge. The base opening may also be very narrow.

The Topsheet/Acquisition Layer/Tissue Layer Laminate

Figure 13:
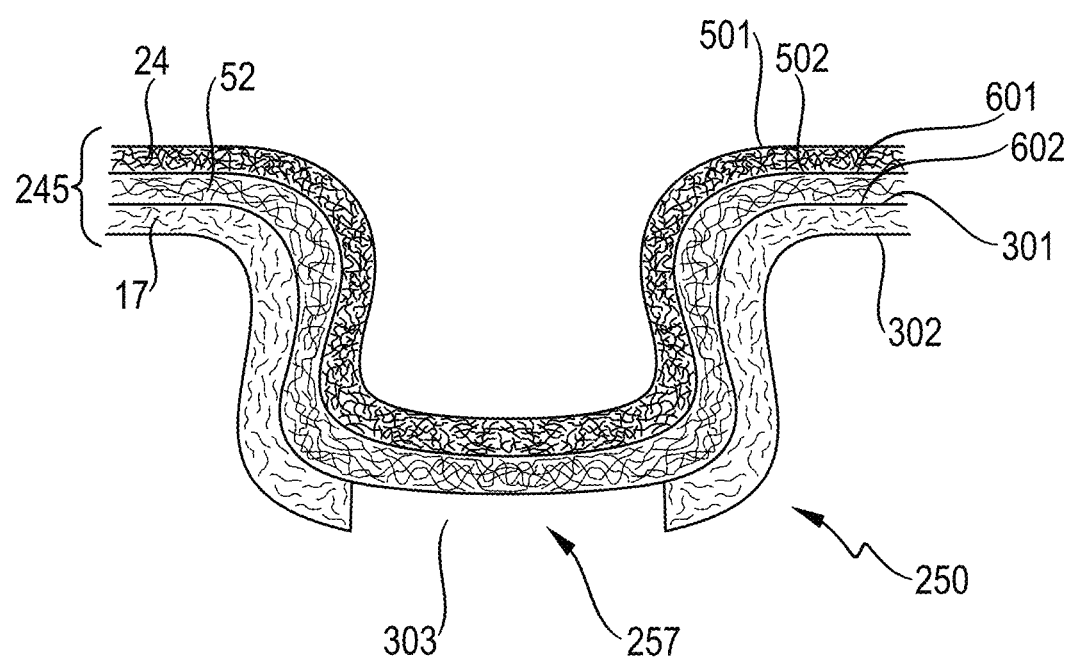
FIG. 13 is a schematic view of an example of a three-dimensional protrusion of the three-dimensional substrate comprising three layers in accordance with the present invention.

Referring to FIG. 13, the three-dimensional substrate 240 may be a laminate 245 comprising three layers in a face to face relationship.

The first layer 246 is the acquisition layer 52, the second layer is the tissue layer 17 and the third layer 247 is the topsheet 24.

The layers of the laminate 145 are in a face to face relationship. The three-dimensional substrate 240 may be a topsheet/acquisition layer/tissue layer laminate 245.

The liquid permeable topsheet 24. i.e. the third layer has a first surface 501 and a second surface 502. The acquisition layer 52 i.e. the first layer has a first surface 601 and second surface 602. The tissue layer 17 i.e. the second layer has a first surface 301 and a second surface 302.

The third layer 247, i.e. the topsheet 24, the first layer 246, i.e. the acquisition layer 52 and the second layer, i.e. the tissue layer 17 are aligned in a face to face relationship.

The second surface 502 of the third layer 247, i.e. the topsheet is in contact with the first surface 601 of the first layer 246, i.e. the acquisition layer.

The second surface 602 of the first layer 246, i.e. the acquisition layer is in contact with the first surface 301 of the second layer, i.e. the tissue layer 17.

The topsheet 24, the acquisition layer 52 and the tissue layer 17 can be simultaneously mechanically deformed and combined together to provide the topsheet/acquisition layer/tissue layer laminate 245 having three-dimensional protrusions 250. This means that the topsheet 24, the acquisition layer 52 and the tissue layer 17 can be mechanically deformed and combined together at the same time during the process.

The process detail above is used to form the topsheet/acquisition layer/tissue layer laminate 245.

The three-dimensional protrusions 250 are formed from the fibers of the topsheet 24, the fibers of the acquisition layer 52 and the fibers of the tissue layer 17.

The three-dimensional protrusions 250 have the same structure and the same characteristics as described above.

Figure 14:
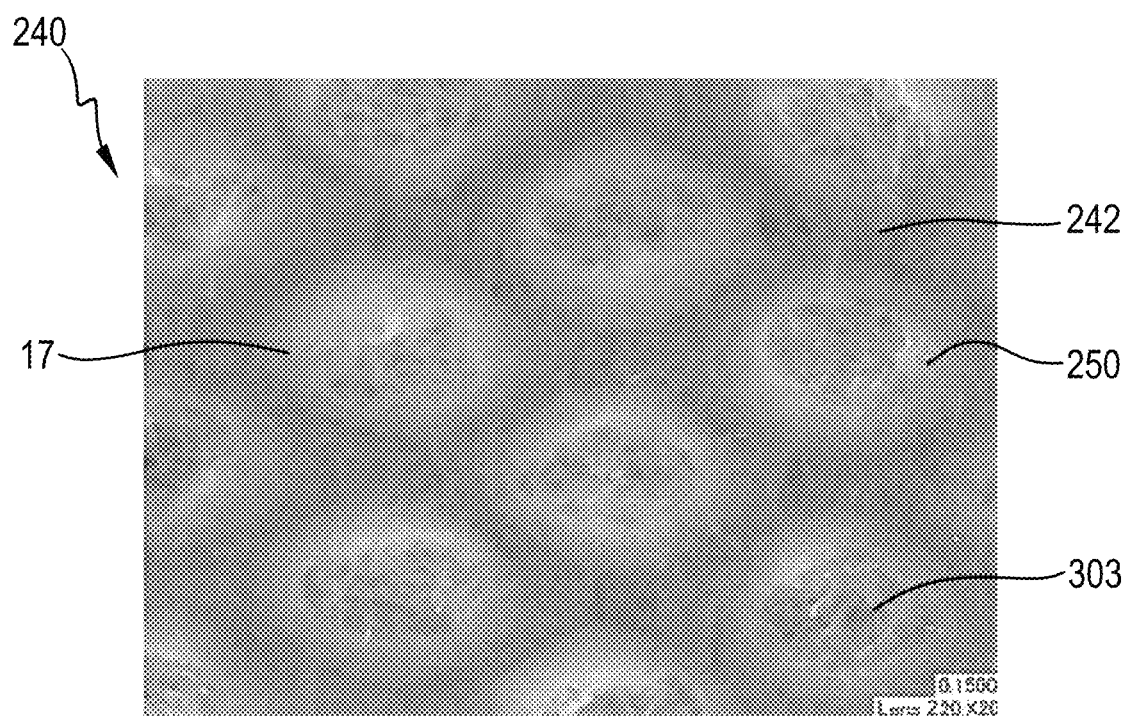
FIG. 14 is a topography image of an example of the three-dimensional substrate comprising three layers in accordance with the present invention.

FIG. 14 is a topographical image of the three-dimensional substrate 240 that is topsheet/acquisition layer/tissue layers laminate 245 comprising three-dimensional protrusions 250. The three-dimensional substrate 240 comprises holes 303 formed in the tissue layer 17 at the opposed distal portions 257 of the majority of the three-dimensional protrusions 250, as shown in FIGS. 13 and 14.

The acquisition layer 52 i.e. the first layer 246 and the topsheet 24 i.e. the third layer 247 do not comprise holes at the opposed distal portions 257 of the three-dimensional protrusions 250.

When the three-dimensional substrate described herein is incorporated into an absorbent article, at the opposed distal portions 257 of the three-dimensional protrusions 250, the acquisition layer 52 can be brought in direct contact with the underlying layer leading to a faster flow of liquid from the first layer 246 (and from the third layer 247 if present) through the underlying layer to the absorbent core 28.

General Description of the Absorbent Article 20

Figure 15:
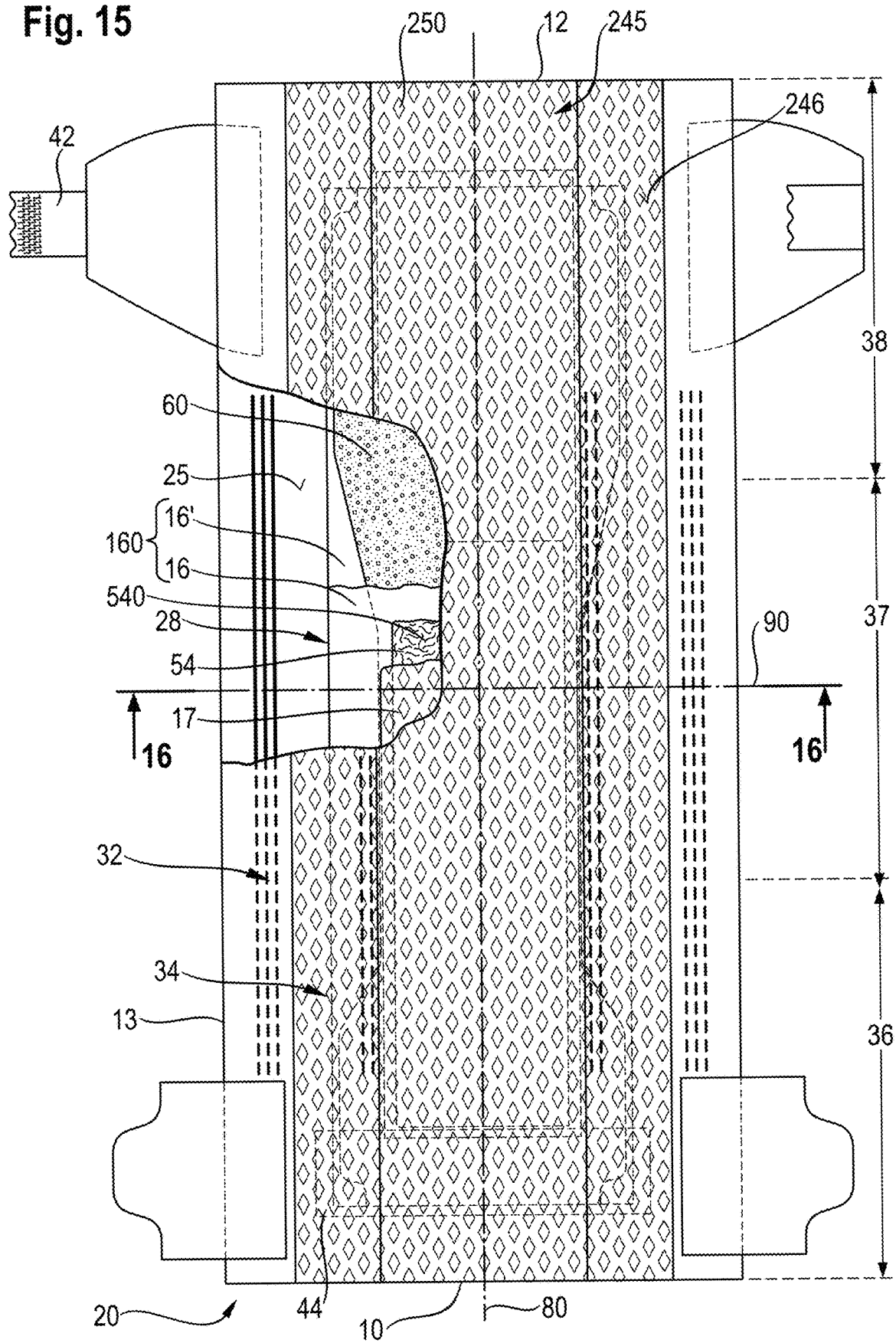
FIG. 15 is an absorbent article in the form of a diaper comprising the three-dimensional substrate according to the invention with some layers partially removed to show internal structures (or elements).
Figure 16:
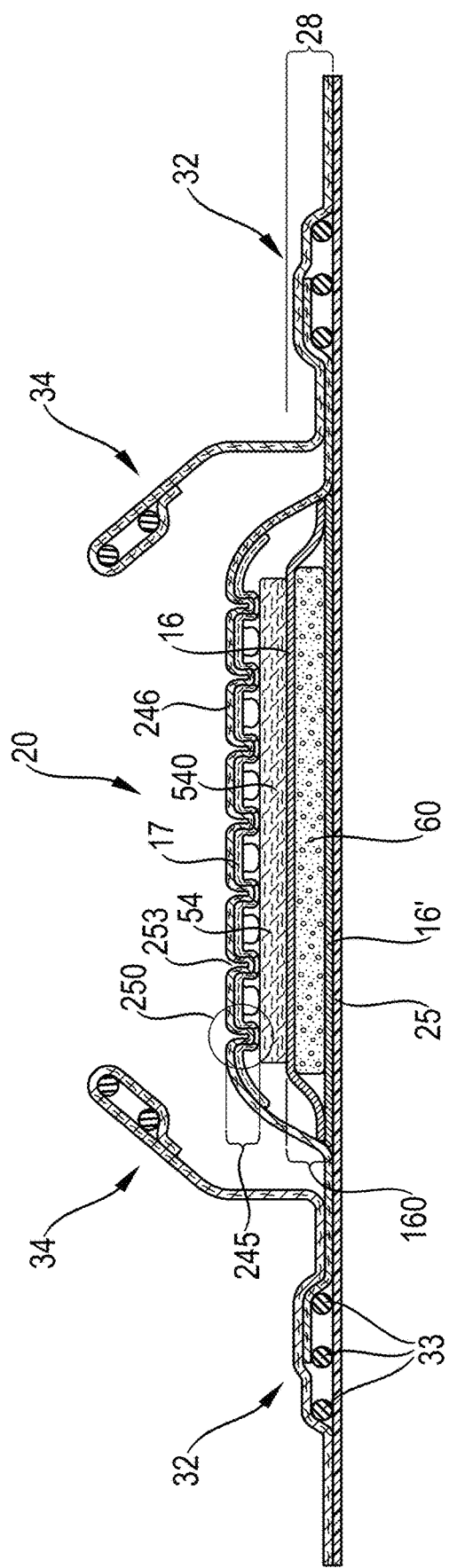
FIG. 16 is a transversal cross-section of the diaper taken along line 16-16 of FIG. 15.
Figure 17:
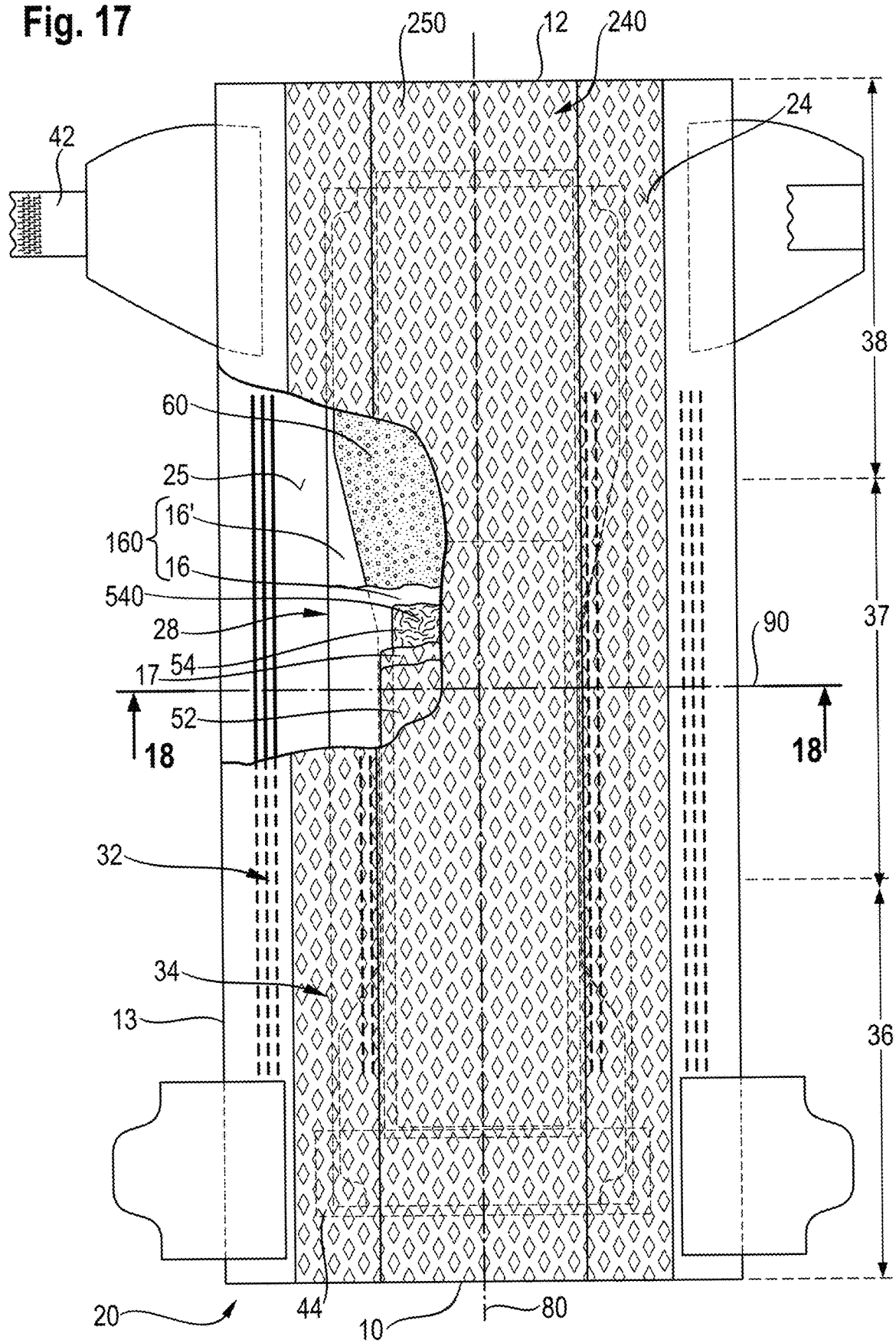
FIG. 17 is an absorbent article in the form of a diaper comprising the three-dimensional substrate comprising three layers according to the invention with some layers partially removed to show internal structures (or elements).
Figure 18:
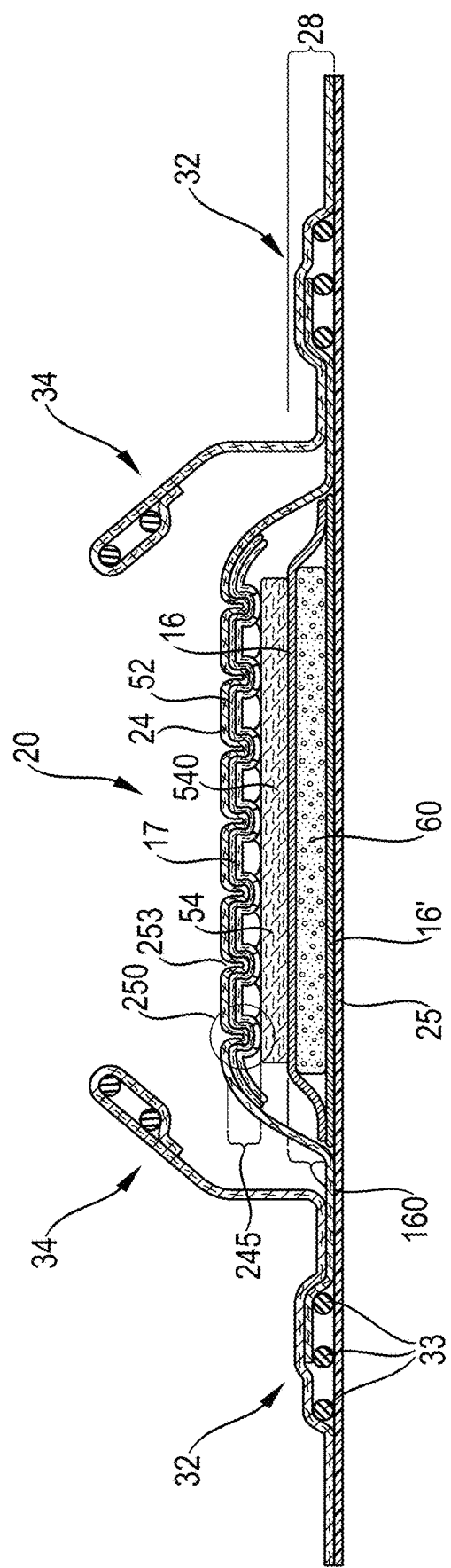
FIG. 18 is a transversal cross section of the diaper taken along line 18-18 of FIG. 17.
Figure 19:
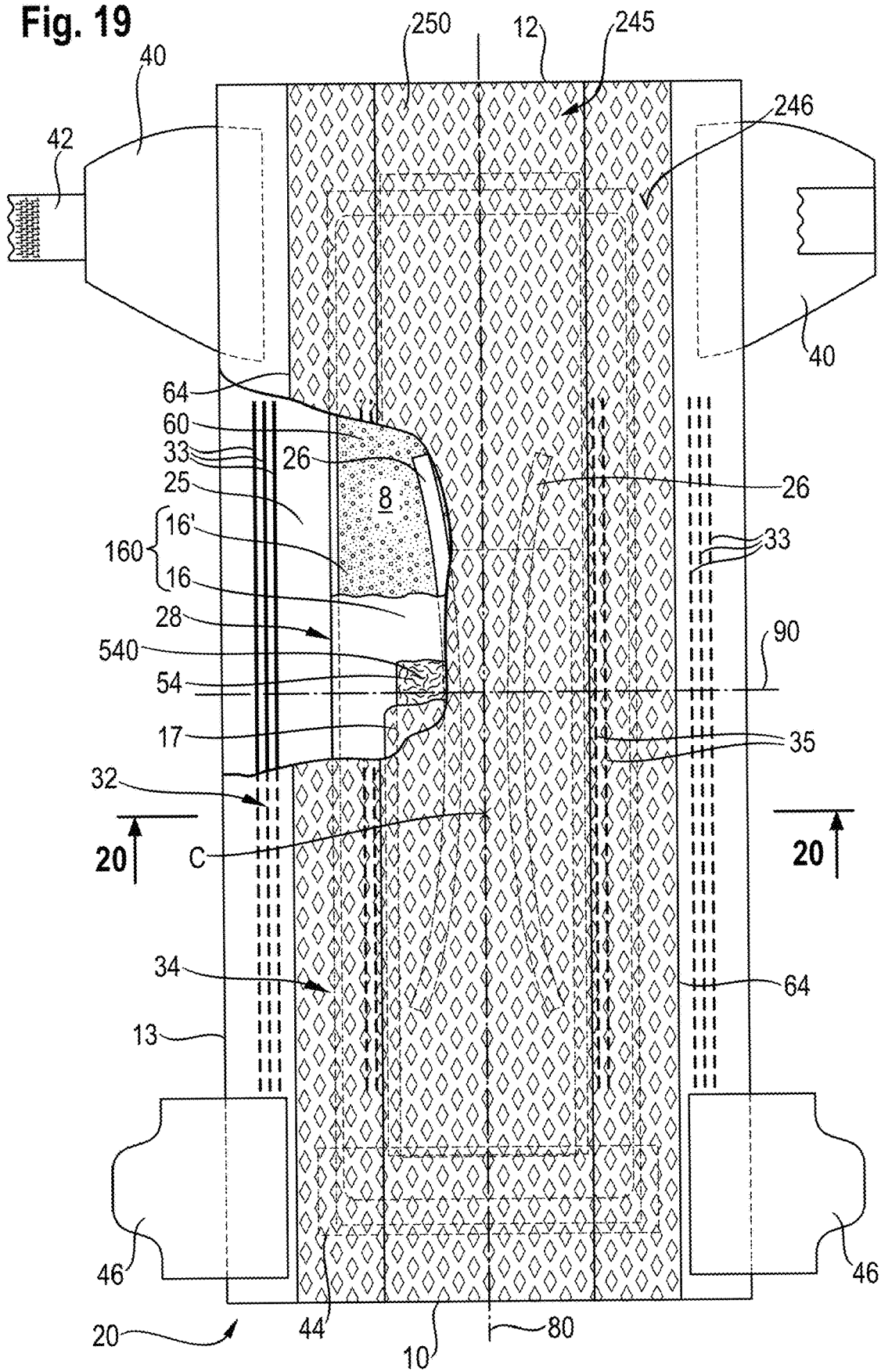
FIG. 19 is an absorbent article in the form of a diaper comprising the three-dimensional substrate with another type of absorbent core according to the invention with some layers partially removed to show internal structures (or elements).

An exemplary absorbent article 20 in which the three-dimensional substrate 240 of the invention can be used is represented in FIGS. 15 to 21 with a different absorbent core construction. FIG. 15; FIG. 17 and FIG. 19 are top plan views of the exemplary diaper 20, in a flat-out state, with portions of the structure being cut-away to more clearly show the construction of the diaper 20. This diaper 20 is shown for illustration purpose only as the invention may be used for making a wide variety of diapers or other absorbent articles.

The absorbent article 20 comprises the three-dimensional substrate 240 that is a laminate 245 comprising at least two layers in a face to face relationship.

According to FIG. 15, the laminate 245 is formed from at least a first layer 246 and a tissue layer 17 as a second layer. In other words, the absorbent article 20 comprises a first layer 246 which may be a liquid permeable topsheet 24 or an acquisition layer 52, and comprises a tissue layer 17 wherein the first layer 246 and the tissue layer 17 are joined to form a laminate 245.

The absorbent article 20 also comprises a liquid impermeable backsheet 25 and an absorbent core 28 between the laminate 245 and the backsheet 25.

The absorbent article 20 comprises a front edge 10, a back edge 12, and two longitudinal side edges 13. The front edge 10 is the edge of the absorbent article 20 which is intended to be placed towards the front of the user when worn, and the back edge 12 is the opposite edge. The absorbent article 20 comprises a longitudinal axis 80 and a transversal axis 90. The absorbent article 20 may be notionally divided by the longitudinal axis 80 extending from the front edge 10 to the back edge 12 of the absorbent article 20 and dividing the absorbent article 20 in two substantially symmetrical halves relative to this axis, when viewing the absorbent article 20 from the wearer facing side in a flat out configuration, as exemplarily shown in FIG. 15, FIG. 17 and FIG. 19.

The absorbent article 20 may comprise elasticized gasketing cuffs 32.

The absorbent article 20 may comprise a distribution layer 54 which may comprise a dry-laid fibrous structure or a wet-laid fibrous structure. The laminate 245 is facing towards the body of the wearer when the absorbent article is in use.

The distribution layer 54 may comprise a dry-laid fibrous structure. The dry-laid fibrous structure may comprise dry-laid fibers 540. The dry-laid fibrous structure may comprise a mixture including dry-laid fibers and superabsorbent polymers. The dry-laid fibers may comprise intra-fiber cross-linked cellulosic fibers.

The distribution layer 54 may comprise a wet-laid fibrous structure. The wet-laid fibrous structure may comprise wet-laid fibers.

The distribution layer 54 may have an average basis weight of from 30 to 400 gsm, in particular from 100 to 300 gsm or from 50 to 250 gsm.

The distribution layer 54 may comprise a dry-laid fibrous structure and/or a wet-laid fibrous structure located between the laminate 245 and the absorbent core 28.

The laminate 245 may be in close contact with the underlying layer, i.e. the optional distribution layer 54 or the absorbent core 28, which allows the liquid bodily exudates to flow from the laminate 245 through the acquisition layer 52 to the absorbent core 28 efficiently.

A carrier layer may be disposed between the three-dimensional substrate 240 and the distribution layer 54. When the distribution layer 54 comprises a dry-laid fibrous structure, the fibers 540 of the dry-laid fibrous structure may pass through the holes 303 formed in the tissue layer 17 and through interruptions that may be present unintentionally in the first layer 246 of the laminate 245. The dry-laid fibers may contact undesirably the skin of the wearer. The carrier layer may act as a barrier layer to impede the fibers 540 of dry-laid fibrous structure from passing through the laminate 245. Also, the carrier layer may help the transfer of the liquid bodily exudates from the laminate 245 to the dry-laid fibrous structure.

Alternatively, the carrier layer may be disposed between the distribution layer 54 and the absorbent core 28. Hence, the carrier layer may help to distribute and transfer of the liquid bodily exudates from the distribution layer 54 to the absorbent core 28 which enables more efficient use of the absorbent core 28.

The carrier layer may be selected from the group consisting of nonwovens, or films and combinations thereof.

Examples of a nonwoven web used for the carrier layer may include various types of known nonwoven webs such as a spunbonded nonwoven web, a meltblown nonwoven web, an a spunbond-meltblown-spunbond nonwoven web. These nonwoven webs are made of thermoplastic polymers.

A material for fibers composing the nonwoven web used for the carrier layer may include various types of known fibers such as polyethylene, polypropylene, polyester, and acryl, conjugate fibers such as polyethylene/polypropylene, polyethylene/polyethylene terephthalate, and polypropylene/polyethylene terephthalate, i.e., fibers formed of core-in-sheath fibers and side-by-side fibers. The fibers may be used alone or in combination. Further, the carrier layer may have a monolayer structure or a multilayer structure.

The carrier layer may also be made of wet-laid fibers. However, the carrier layer is distinct from the second layer, i.e. the tissue layer.

The carrier layer may have a basis weight of at least 5 gsm to 60 gsm or at least 5 gsm to 20 gsm or at least 5 to 15 gsm.

As already explained above, the laminate 245 comprises the first layer 246 and the tissue layer 17 in a face to face relationship. The laminate 245 comprises three-dimensional protrusions 250.

The majority of the three-dimensional protrusions 250 of the laminate 245 may protrude towards the backsheet 25 of the absorbent article.

The majority of the three-dimensional protrusions 250 may be disposed in any suitable arrangement across the land areas of the laminate 245.

Figure 21:
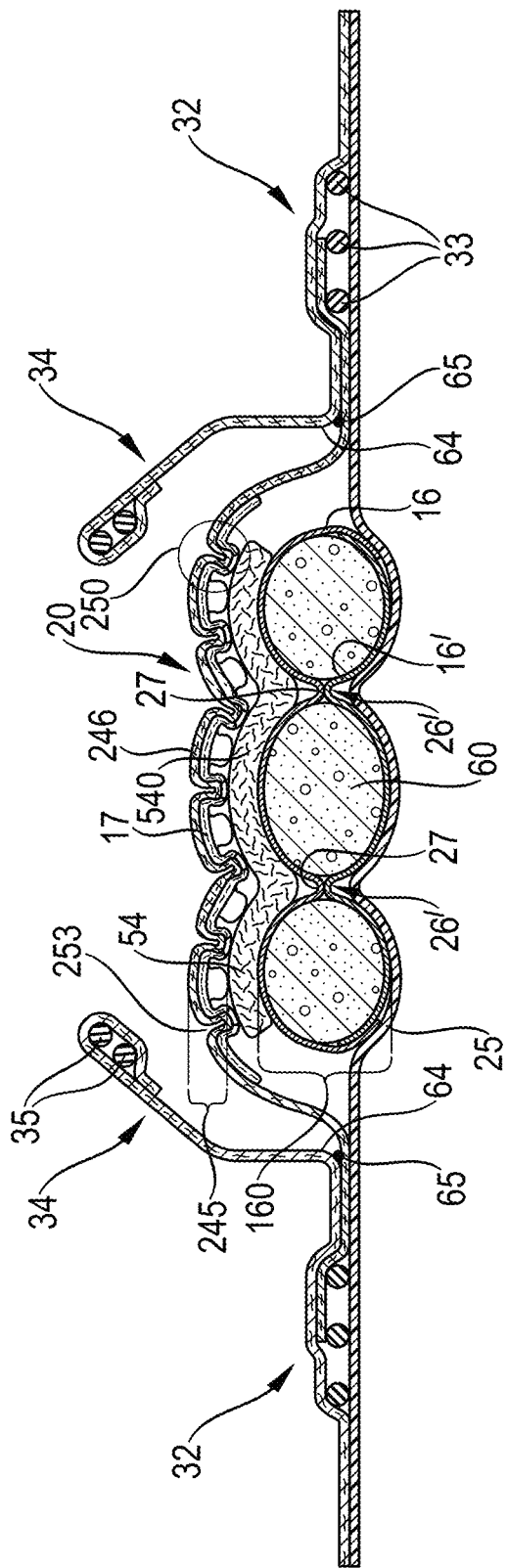
FIG. 21 is a transversal cross-section of the absorbent article of FIG. 19 taken at the same point as FIG. 20 when the absorbent article is loaded with liquid bodily exudates.

The absorbent article 20 may comprise elasticized gasketing cuffs 32 present between the laminate 245 and the backsheet 25 and upstanding barrier leg cuffs 34. As shown in FIG. 21, the barrier leg cuffs 34 may be delimited by a proximal edge 64 joined to the rest of the article, typically the three-dimensional substrate 240 and/or the backsheet 25, and a free terminal edge intended to contact and form a seal with the wearer's skin. The barrier leg cuffs 34 may be joined at the proximal edge 64 by a bond 65 which may be made for example by adhesive bonding, fusion bonding or combination of known bonding means. Each barrier leg cuff 34 may comprise one, two or more elastic strings 35 to provide a better seal. The gasketing cuffs 32 may be placed laterally outwardly relative to the barrier leg cuffs 34. The gasketing cuffs 32 can provide a better seal around the thighs of the wearer. Usually each gasketing leg cuff 32 will comprise one or more elastic string or elastic element 33 for example between the laminate and backsheet in the area of the leg openings.

FIGS. 15, 17 and 19 also show other typical diaper components such as a fastening system comprising fastening tabs 42 attached towards the back edge 12 of the absorbent article 20 and cooperating with a landing zone 44 towards the front edge 10 of the absorbent article 20. As shown on FIG. 19, the absorbent article 20 may also comprise front ears 46 and back ears 40 as it is known in the art.

The absorbent article 20 may also comprise other typical components, which are not represented in the Figures, such as a back elastic waist feature, a front elastic waist feature, transverse barrier cuff(s), etc.

The absorbent article 20 can also be notionally divided by the transversal axis 90 in a front region and a back region of equal length measured on the longitudinal axis, when the absorbent article 20 is in a flat state. The absorbent article's transversal axis 90 is perpendicular to the longitudinal axis 80 and placed at half the length of the absorbent article 20. The length of the absorbent article 20 can be measured along the longitudinal axis 80 from the front edge 10 to the back edge 12 of the absorbent article 20. The three-dimensional substrate 240, distribution layer 54 and absorbent core 28 each have a width which can be measured from their respective longitudinal edges and in parallel to the transversal axis 90.

The absorbent article 20 is notionally divided in a front region 36, a back region 38 and a crotch region 37 located between the front and the back region of the absorbent article 20. Each of the front, back and crotch region is ⅓ of the length of the absorbent article 20 in a direction parallel to the longitudinal axis.

The tissue layer 17 in the laminate 245 may be positioned in the front region 36, in the crotch region 37 and in the back region 38 of the absorbent article 20.

The tissue layer 17 in the laminate 245 may be only positioned in the front region 36 and in the crotch region 37 of the absorbent article 20.

The tissue layer 17 in the laminate 245 may be only positioned in the back region 38 and in the crotch region 37 of the absorbent article 20.

The absorbent core 28 of the present invention may comprise as absorbent material 60 a blend of cellulosic fibers (so called "airfelt") and superabsorbent polymers in particulate form encapsulated in one or more substrates, see for example U.S. Pat. No. 5,151,092 (Buell). Alternatively, the absorbent core 28 may be airfelt free as described in detail below.

The term "absorbent core" does not include an acquisition or distribution layer or any other component of an absorbent article which is not either an integral part of the core wrap or placed within the core wrap. The absorbent core is typically the component of an absorbent article which has the highest absorbent capacity of all the components of the absorbent article.

Generally, the absorbent core 28 can be defined by the periphery of the layer formed by the absorbent material 60 within the core wrap 160, as seen from the top side of the absorbent core 28. The absorbent core 28 can take various shapes, in particular display a so-called "dog bone" or "hour-glass" shape, which shows a tapering along its width towards the middle or "crotch" region of the core. In this way, the absorbent core 28 may have a relatively narrow width in an area of the absorbent core 28 intended to be placed in the crotch region of the absorbent article. This may provide for example better wearing comfort. The absorbent core 28 may thus have a width (as measured in the transversal direction) at its narrowest point which is less than about 100 mm, 90 mm, 80 mm, 70 mm, 60 mm or even less than about 50 mm. The absorbent core 28 can also be generally rectangular, see for example as shown in FIG. 19, but other deposition areas can also be used such as a 'T' or "Y" or "hour-glass" or "dog-bone" shape.

FIG. 17 is a top plan view of the exemplary diaper 20 which comprises the three-dimensional substrate 240 with three layers. FIG. 18 is transversal cross-section of the absorbent article 20 taken along line 18-18 of FIG. 17, which comprises the three-dimensional substrate 240 with three-layers.

According to FIG. 17 and FIG. 18, the absorbent article 20 comprises a topsheet/acquisition layer/tissue layer laminate 245 formed from a liquid permeable topsheet 24, an acquisition layer 52 and a tissue layer 17. The acquisition layer 52 is positioned between the topsheet 24 and the tissue layer 17. In other words, the absorbent article 20 comprises a liquid permeable topsheet 24, an acquisition layer 52 and a tissue layer 17 wherein the topsheet 24, the acquisition layer 52 and the tissue layer are joined to form a topsheet/acquisition layer/tissue layer laminate 245.

As explained in more detail above, the topsheet/acquisition layer/tissue layer laminate 245 comprises the topsheet 24, the acquisition layer 52 and the tissue layer 17 in a face to face relationship.

The acquisition layer 52 can receive the liquid bodily exudates that pass through the topsheet 24 and can distribute them to the tissue layer which will distribute them to underlying absorbent layers. The acquisition layer 52 can also receive the liquid bodily exudates that pass through the topsheet 24 and can distribute them to underlying absorbent layers where there are holes 303 in the tissue layer 17 at the opposed distal portions of the majority of the three-dimensional protrusions. The topsheet 24 of the topsheet/acquisition layer/tissue layer laminate 245 can be readily dewatered.

The topsheet 24 in the topsheet/acquisition layer laminate 245 may be less hydrophilic than the acquisition layer 52. In order to enhance dewatering of the topsheet 24 of the topsheet/acquisition layer/tissue layer laminate 245, the pore size of the acquisition layer 52 may be reduced. For this, the acquisition layer 52 may made of fibers with relatively small denier. The acquisition layer 52 may also have an increased density.

The absorbent article may also comprise a distribution layer 54 that is facing toward the tissue layer of the topsheet/acquisition layer/tissue layer laminate 245.

A width of the acquisition layer 52 and the tissue layer 17 in a direction parallel to the transversal axis 90 may be less than a width of the topsheet 24 in a direction parallel to the transversal axis 90 of the absorbent article 20. If the width of the topsheet 24, the acquisition layer 52 and the tissue layer 17 were the same, wicking of the liquid bodily exudates underneath the gasketing cuffs 32 might occur. Hence, the liquid bodily exudates might not be properly absorbed by the absorbent core 28, which may lead to leakage of the liquid bodily exudates out of the absorbent article. If the width of the acquisition layer 52 and the tissue layer 17 in a direction parallel to the transversal axis 90 is less that the width of the topsheet in a direction parallel to the transversal axis 90, the acquisition layer 52 and the tissue layer 17, which may receive the liquid bodily exudates from the topsheet 24, can directly transmit the liquid bodily exudates to the distribution layer 54 or to the absorbent core 28. Hence, the liquid bodily exudates temporary stored in the acquisition layer 52 and the tissue layer 17 of the laminate 245 will not readily be drawn towards and underneath the gasketing cuffs 32 by capillary forces. Leakage can thus be reduced by having the width of the acquisition layer 52 and the tissue layer 17 in a direction parallel to the transversal axis 90 less that the width of the topsheet 24 in the laminate 245 in a direction parallel to the transversal axis 90.

A width of the acquisition layer 52 in a direction parallel to the transversal axis 90 may be the same as a width of the tissue layer 17 in a direction parallel to the transversal axis 90 of the absorbent article 20.

A width of the acquisition layer 52 in a direction parallel to the transversal axis 90 may be larger than a width of the tissue layer 17 in a direction parallel to the transversal axis 90 of the absorbent article 20.

The width of the tissue layer 17 and the acquisition layer 52 in a direction parallel to the transversal axis 90 of the laminate 245 may not be more than 40% wider than the width of the optional distribution layer 54 and/or more than 20% wider than the width of the absorbent core 28 in a direction parallel to the transversal axis 90. In that case, the liquid bodily exudates may not accumulate at or adjacent to the longitudinal edges of the acquisition layer. Indeed, when the acquisition layer 52 and the tissue layer 17 of the laminate 245 is no more than 20% wider than the width of the absorbent core 28, the liquid bodily exudates can readily be transported into the absorbent core 28, which can efficiently drain the fluid from the acquisition layer 52 and the tissue layer 17 into the absorbent core 28.

A portion of the backsheet 25 may be joined to the topsheet 24 at or adjacent to the longitudinal edges of the first surface of the topsheet/acquisition web laminate 245 in the cross direction. The longitudinal edges of the first surface of the topsheet/acquisition web laminate 245 do not comprise any acquisition layer 52 or tissue layer 17. When a portion of the backsheet 25 is joined to a portion of the topsheet 24 of the topsheet/acquisition web laminate 245, the acquisition layer 52 and the tissue layer 17 is then enveloped between the topsheet 24 and the backsheet 25.

The length of the acquisition layer 52 and of the tissue layer 17 in the topsheet/acquisition layer/tissue layer laminate 245 in a direction parallel to the longitudinal axis may be less than the length of the topsheet 24 taken along the longitudinal axis 80 of the absorbent article 20, in a direction parallel to the longitudinal axis, as shown in FIG. 19. When the length of the acquisition layer 52 in the topsheet/acquisition layer/tissue layer laminate 245 is less than the length of the topsheet 24, the liquid bodily exudates cannot be readily drawn towards the lateral edges 10, 12 of the absorbent article 20, which reduces leakage.

A length of the acquisition layer 52 in a direction parallel to the transversal axis 90 may be the same as a length of the tissue layer 17 in a direction parallel to the transversal axis 90 of the absorbent article 20.

A length of the acquisition layer 52 in a direction parallel to the transversal axis 90 may be larger than a length of the tissue layer 17 in a direction parallel to the transversal axis 90 of the absorbent article 20.

The length of the acquisition layer 52 in the topsheet/acquisition layer/tissue layer laminate 245 may be less than the length of the absorbent core 28 taken along the longitudinal axis 80 of the absorbent article 20.

The acquisition layer 52 and the tissue layer 17 in the topsheet/acquisition layer/tissue layer laminate 245 may be positioned in the front region 36, in the crotch region 37 and in the back region 38 of the absorbent article 20.

The acquisition layer 52 and the tissue layer 17 in the topsheet/acquisition layer/tissue layer laminate 245 may be positioned in the front region 36 and in the crotch region 37 of the absorbent article 20. Such arrangement can help to acquire and distribute the liquid bodily exudates such as urine, around the pee point where liquid is initially introduced into the absorbent article 20.

The acquisition layer 52 and the tissue layer 17 in the topsheet/acquisition layer/tissue layer laminate 245 may be positioned in the back region 38 and in the crotch region 37 of the absorbent article 20. Such arrangement can help to acquire the feces of the wearer, especially when the feces have a low viscosity.

The topsheet/acquisition layer/tissue layer laminate 245 comprises three-dimensional protrusions 250.

The majority of the three-dimensional protrusions 250 of the laminate 245 may at least be present in the area where the topsheet 24 overlaps the acquisition layer 52 and the tissue layer 17 in the laminate 245. However, the majority of the three-dimensional protrusions 250 of the laminate 245 may be present in the area where there is only the topsheet 24 and where there is no overlap between the topsheet 24 and the acquisition layer 52 and the tissue layer 17. In that case, the majority of the three-dimensional protrusions 250 which are formed in the topsheet 24 of the laminate 245 are formed from the fibers of the topsheet 24.

The length of the area of the majority of the three-dimensional protrusions 250 of the laminate 245 may be from 5% to 60% or from 10% to 40% wider than the length of the acquisition layer 52 and of the tissue layer 17 of the laminate 245.

In another alternative, the majority of the three-dimensional protrusions 250 of the laminate 245 may only be present where the topsheet 24 overlaps the acquisition layer 52 and the tissue layer 17 in the laminate 245.

The absorbent article 20 of FIG. 17 comprises the other elements that are described above.

Some components of the absorbent article 20 will now be discussed in more details.

"Airfelt-Free" Absorbent Core 28

The absorbent core 28 of the absorbent article 20 may comprise an absorbent material 60 enclosed within a core wrap 160. The absorbent material 60 may comprise from 80% to 100% of SAP, such as SAP particles, by total weight of the absorbent material 60. The core wrap 160 is not considered as an absorbent material 60 for the purpose of assessing the percentage of SAP in the absorbent core 28.

The term "superabsorbent polymers" (herein abbreviated as "SAP") as used herein refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP of the invention may in particular have a CRC value of more than 20 g/g, or more than 25 g/g, or from 20 to 50 g/g, or from 20 to 40 g/g, or 25 to 35 g/g.

By "absorbent material" it is meant a material which has at least some absorbency and/or liquid retaining properties, such as SAP, cellulosic fibers as well as some hydrophilically treated synthetic fibers. Typically, adhesives used in making absorbent cores have no absorbency properties and are not considered as absorbent material. The SAP content may be substantially higher than 80%, for example at least 85%, at least 90%, at least 95% and even up to and including 100% of the weight of the absorbent material 60 contained within the core wrap 160. This above SAP content substantially higher than 80% SAP may provide a relatively thin absorbent core 28 compared to conventional absorbent cores typically comprising between 40-60% SAP and 40-60% of cellulosic fibers. The absorbent material 60 of the invention may in particular comprise less than 10% weight percent, or less than 5% weight percent, or even be substantially free of natural and/or synthetic fibers. The absorbent material 60 may advantageously comprise little or no cellulosic fibers, in particular the absorbent core 28 may comprise less than 15%, 10%, or 5% (airfelt) cellulosic fibers by weight of the absorbent core 28, or even be substantially free of cellulose fibers. Such absorbent core 28 may be relatively thin and thinner than conventional airfelt cores. FIG. 15, FIG. 16, FIG. 17 and FIG. 18 are illustrations of an absorbent article 20 comprising an "airfelt-free" absorbent core 28.

The absorbent material 60 may comprise at least 80% of superabsorbent polymers or at least 95% of superabsorbent polymers, by total weight of the absorbent material.

"Airfelt-free" absorbent cores 28 comprising relatively high amount of SAP with various absorbent core designs have been proposed in the past, see for example in U.S. Pat. No. 5,599,335 (Goldman), EP1447066A1 (Busam), WO95/11652 (Tanzer), U.S. Pat. Publ. No. 2008/0312622A1 (Hundort), and WO2012/052172 (Van Malderen).

The absorbent core 28 of the invention may comprise adhesive for example to help immobilizing the SAP within the core wrap 160 and/or to ensure integrity of the core wrap, 160 in particular when the core wrap 160 is made of one or more substrates. The core wrap 160 will typically extend over a larger area than strictly needed for containing the absorbent material 60 within.

Core Wrap 160

The absorbent material 60 is encapsulated in one or more substrates. The core wrap 160 comprises a top side 16 facing the laminate 245 and a bottom side 16' facing the backsheet 25. The core wrap 160 may be made of a single substrate folded around the absorbent material 60. The core wrap 160 may be made of two substrates (one mainly providing the top side 16 and the other mainly providing the bottom side 16') which are attached to another, as exemplarily shown in FIG. 17. Typical configurations are the so-called C-wrap and/or sandwich wrap. In a C-wrap, as exemplarily shown in FIG. 20, the longitudinal and/or transversal edges of one of the substrate are folded over the other substrate to form flaps. These flaps are then bonded to the external surface of the other substrate, typically by bonding with an adhesive. The so called C-wrap construction can provide benefits such as improved resistance to bursting in a wet loaded state compared to a sandwich seal.

The core wrap 160 may be formed by any materials suitable for receiving and containing the absorbent material 60. The core wrap 160 may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, U.S. Pat. Appl. Publ. Nos. 2011/0268932A1, 2011/0319848A1, or 2011/0250413A1. Nonwoven materials provided from synthetic fibers may be used, such as polyethylene (PE), polyethylene terephthalate (PET) and in particular polypropylene (PP).

"Airfelt-Free" Absorbent Core 28 Comprising Substantially Absorbent Material Free Areas 26

The term "substantially free of absorbent material" or "substantially absorbent material free" as used herein means that the basis weight of the absorbent material in the substantially absorbent material free areas is at least less than 10%, in particular less than 5%, or less than 2%, of the basis weight of the absorbent material in the rest of the absorbent core.

As shown in FIG. 19, the absorbent core 28 may comprise an absorbent material deposition area 8 defined by the periphery of the layer formed by the absorbent material 60 within the core wrap 160.

Figure 20:
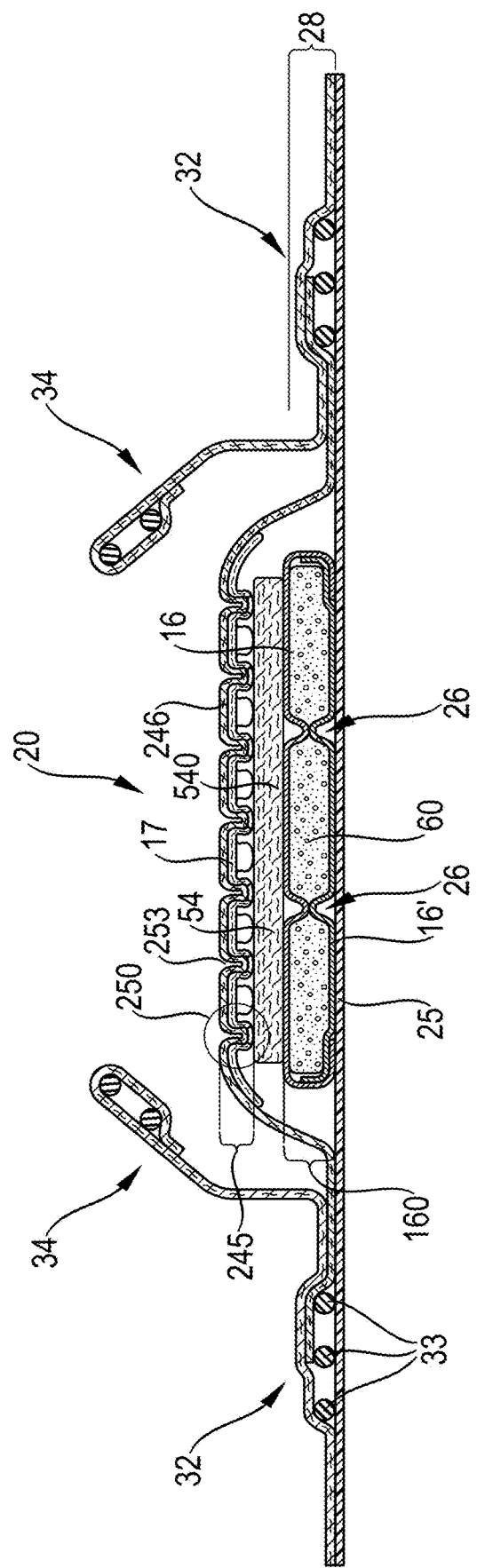
FIG. 20 is a transversal cross-section of a diaper taken along line 20-20 of FIG. 19.

The absorbent core 28 may comprise one or more substantially absorbent material free area(s) 26 which is/are substantially free of absorbent material 60 and through which a portion of the top side 16 of the core wrap 160 is attached by one or more core wrap bond(s) 27 to a portion of the bottom side 16' of the core wrap 160, as shown in FIGS. 19, 20 and 21. In particular, there can be no absorbent material 60 in these areas. Minimal amount such as contaminations with absorbent material 60 that may occur during the making process are not considered as absorbent material 60. The one or more substantially absorbent material free area(s) 26 is/are advantageously confined by the absorbent material 60, which means that the substantially absorbent material free area(s) 26 do(es) not extend to any of the edge of the absorbent material deposition area 8.

If the substantially absorbent material free area 26 extends to any of the edges of the absorbent material deposition area 8, each substantially absorbent material free area 26 may have areas of absorbent material 60 on either side of each substantially absorbent material free area 26.

The absorbent core 28 may comprise at least two substantially absorbent material free areas 26 symmetrically disposed on both sides of the longitudinal axis of the absorbent core 28, as shown in FIG. 19.

The substantially absorbent material free area(s) 26 may be straight and completely oriented longitudinally and parallel to the longitudinal axis but also may be curved or have one or more curved portions.

Furthermore, in order to reduce the risk of liquid bodily exudate leakages, the substantially absorbent material free area(s) 26 advantageously do not extend up to any of the edges of the absorbent material deposition area 8, and are therefore surrounded by and fully encompassed within the absorbent material deposition area 8 of the absorbent core 28. Typically, the smallest distance between a substantially absorbent material free area 26 and the closest edge of the absorbent material deposition area 8 is at least 5 mm.

"Airfelt free" absorbent cores 28 comprising substantially absorbent material free areas 26 have been proposed, see for example in EP Patent Application No. 12196341.7.

As shown in FIG. 21, one or more channel(s) 26' along the substantially absorbent material free area(s) 26 in the absorbent core 28 may start forming when the absorbent material 60 absorbs a liquid and starts swelling. As the absorbent core 28 absorbs more liquid, the depressions within the absorbent core 28 formed by the channel(s) 26' will become deeper and more apparent to the eye and the touch. The formation of the channel(s) 26' may also serve to indicate that the absorbent article 20 has been loaded with liquid bodily exudates. The core wrap bond(s) 27 should remain substantially intact at least during a first phase as the absorbent material 60 absorbs a moderate quantity of liquid bodily exudates.

As shown in FIG. 21, when the absorbent material swells, the core wrap bonds 27 remain at least initially attached in the substantially absorbent material free areas 26. The absorbent material 60 swells in the rest of the absorbent core 28 when it absorbs a liquid, so the core wrap thus forms channels 26' along the substantially absorbent material free areas 26 comprising the core wrap bonds 27.

Example

Prototype of the Laminate:

The topsheet is a hydrophilic coated bicomponent PE/PP sheath/core spunbond nonwoven material with a basis weight of 20 gsm. The acquisition layer is a hydrophilic coated 43 gsm resin-bonded carded nonwoven consisting of 30% styrene butadiene latex binder and 70% fiber mix. The fiber mix contains a 40:60 mixture of 6 denier solid round PET fibers and 9 denier solid round PET fibers respectively.

The tissue layer is a wet-laid fibrous substrate made through the use of a patterned papermaking belt 300 for forming three-dimensionally structured wet-laid and wet-formed webs as described in U.S. Pat. No. 4,637,859, issued Jan. 20, 1987, to Trokhan. The basis weight of the tissue layer was 42.6 gsm and a total dry tensile strength of 1947 g/in measured according to the Total Dry Tensile strength Test Method.

The topsheet and the acquisition layer are attached to each other with a hot melt adhesive applied in the form of spirals with a basis weight of 2 gsm, and the acquisition layer and the tissue layer are attached to each other with a hot melt adhesive applied in the form of spirals with a basis weight of 4.5 gsm, to form a topsheet/acquisition layer/tissue laminate. The laminate is constructed such that each of the layers was oriented in the same direction and overlapped with one another.

The topsheet, the acquisition layer and the tissue layer attached together are simultaneously mechanically deformed by passing them between a pair of intermeshing male and female rolls. The protrusions are created such that the bases of the protrusions are present on the topsheet side (i.e. protrusions oriented towards the garment). The teeth on the male roll have a rounded diamond shape like that shown in FIG. 12A and FIG. 12B, with vertical sidewalls. The teeth are 3.38 mm (0.133 inch) long and 2.77 mm (0.109 inch) wide with a CD spacing of 5.08 mm (0.200 inch) and an MD spacing of 8.79 mm (0.346 inch). The recesses in the mating female roll also had a rounded diamond shape, similar to that of the male roll, with a clearance between the rolls of 0.53-1.09 mm (0.021-0.043 inch). The process speed was approximately 20 m/min and depth of engagement (DOE) was 2.92 mm (0.115 inch), with the topsheet being in contact with the male roll.

Comparative Example 1

It is the same as Example 1 but without the tissue layer comprised in the laminate.

Result:

The opacity has also been measured, according to the opacity test method disclosed below, for the topsheet/acquisition layer/tissue layer laminate according to the invention and for the comparative example 1.

|  | Opacity (in %) |
| --- | --- |
| Example 1 | 74 |
| Comparative example 1 | 45 |

The opacity of the topsheet/acquisition layer/tissue layer laminate according to the invention is better than the opacity for the topsheet/acquisition layer laminate comparative example. Having a three-dimensional substrate comprising a tissue layer may increase the opacity of the laminate.

The post-recovery caliper has also been measured, according to the accelerated compression method disclosed below, for the topsheet/acquisition layer/tissue layer laminate according to the invention and for the comparative example 1.

| Compression (in kPa) | Example 1 | | Comparative Example 1 | |
| --- | --- | --- | --- | --- |
| | Caliper (mm) | Stdev | Caliper (mm) | Stdev |
| None (pre-compression) | 3.12 | 0.10 | 2.12 | 0.14 |
| 4 kPa (post recovery caliper) | 2.28 (73%) | 0.05 | 1.03 (49%) | 0.09 |
| 7 kPa (post recovery caliper) | 2.04 (65%) | 0.05 | 0.90 (42%) | 0.05 |

The post-recovery caliper of the topsheet/acquisition layer/tissue layer laminate according to the invention is higher than the post-recovery caliper for the topsheet/acquisition layer laminate comparative example. Moreover, the percentage of caliper loss after a compression of 4 kPa and a compression of 7 kPa is lower for the topsheet/acquisition layer/tissue layer laminate according to the invention than for the comparative example 1. Having a three-dimensional substrate comprising a tissue layer may increase the caliper of the laminate after being compressed and the laminate according to the invention can thereby have an improved caliper recovery after compression.

Test Methods

Unless otherwise specified, all tests described herein are conducted on samples that have been conditioned at a temperature of 23° C.±2° C. and a relative humidity of 50%±2% for a minimum of 2 hours prior to testing. All tests are conducted under the same environmental conditions. Samples conditioned as described herein are considered dry samples. Further, all tests are conducted in such conditioned room.

Tensile Test Method: Elongation, Tensile Strength, TEA and Modulus

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the cell. Both the movable (upper) and stationary (lower) pneumatic jaws are fitted with smooth stainless steel faced grips, 25.4 mm in height and wider than the width of the test specimen. An air pressure of about 60 psi is supplied to the jaws.

Eight usable units of fibrous substrate are divided into two stacks of four samples each. The samples in each stack are consistently oriented with respect to machine direction (MD) and cross direction (CD). One of the stacks is designated for testing in the MD and the other for CD. Using a one inch precision cutter (Thwing Albert JDC-1-10, or similar) cut 4 MD strips from one stack, and 4 CD strips from the other, with dimensions of 1.00 in ±0.01 in wide by 3.0-4.0 in long. Each strip of one usable unit thick will be treated as a unitary specimen for testing.

Program the tensile tester to perform an extension test, collecting force and extension data at an acquisition rate of 20 Hz as the crosshead raises at a rate of 2.00 in/min (5.08 cm/min) until the specimen breaks. The break sensitivity is set to 80%, i.e., the test is terminated when the measured force drops to 20% of the maximum peak force, after which the crosshead is returned to its original position.

Set the gauge length to 1.00 inch. Zero the crosshead and load cell. \Insert at least 1.0 in of the unitary specimen into the upper grip, aligning it vertically within the upper and lower jaws and close the upper grips. Insert the unitary specimen into the lower grips and close. The unitary specimen should be under enough tension to eliminate any slack, but less than 5.0 g of force on the load cell. Start the tensile tester and data collection. Repeat testing in like fashion for all four CD and four MD unitary specimens.

Program the software to calculate the following from the constructed force (g) verses extension (in) curve:

Tensile Strength is the maximum peak force (g) divided by the sample width (in) and reported as g/in to the nearest 1 g/in.

Adjusted Gauge Length is calculated as the extension measured at 3.0 g of force (in) added to the original gauge length (in).

Elongation is calculated as the extension at maximum peak force (in) divided by the Adjusted Gauge Length (in) multiplied by 100 and reported as % to the nearest 0.1%

Total Energy (TEA) is calculated as the area under the force curve integrated from zero extension to the extension at the maximum peak force (g*in), divided by the product of the adjusted Gauge Length (in) and specimen width (in) and is reported out to the nearest 1 g*in/in².

Replot the force (g) verses extension (in) curve as a force (g) verses strain curve. Strain is herein defined as the extension (in) divided by the Adjusted Gauge Length (in).

Program the software to calculate the following from the constructed force (g) verses strain curve:

Tangent Modulus is calculated as the slope of the linear line drawn between the two data points on the force (g) versus strain curve, where one of the data points used is the first data point recorded after 28 g force, and the other data point used is the first data point recorded after 48 g force. This slope is then divided by the specimen width (2.54 cm) and reported to the nearest 1 g/cm.

The Tensile Strength (g/in), Elongation (%), Total Energy (g*in/in²) and Tangent Modulus (g/cm) are calculated for the four CD unitary specimens and the four MD unitary specimens. Calculate an average for each parameter separately for the CD and MD specimens.

Calculations:

Geometric Mean Tensile=Square Root of [MD Tensile Strength (g/in)×CD Tensile Strength (g/in)]

Geometric Mean Peak Elongation=Square Root of [MD Elongation (%)×CD Elongation (%)]

Geometric Mean TEA=Square Root of [MD TEA (g*in/in²)×CD TEA (g*in/in²)]

Geometric Mean Modulus=Square Root of [MD Modulus (g/cm)×CD Modulus (g/cm)]

Total Dry Tensile Strength (TDT)=MD Tensile Strength (g/in)+CD Tensile Strength (g/in)

Total TEA=MD TEA (g*in/in²)+CD TEA (g*in/in²)

Total Modulus=MD Modulus (g/cm)+CD Modulus (g/cm)

Tensile Ratio=MD Tensile Strength (g/in)/CD Tensile Strength (g/in)

Accelerated Compression Method

1. Cut 6 samples of the topsheet/acquisition layer laminate 245 (called herein specimen) to be tested into a 80 mm MD×minimum 80 mm CD rectangle and 9 samples of paper towel into a 3 inch×4 inch (7.6 cm×10.2 cm) rectangle. The samples that have been conditioned at a temperature of 23° C.±2° C. and a relative humidity of 10% to 30% for a minimum of 2 hours prior to testing.
2. Measure the caliper of each of the 6 specimens at 0.5 kPa and a dwell time of 9 seconds using a Thwing-Albert ProGage Thickness Tester or equivalent with a 50-60 millimeter diameter circular foot. Record the pre-compression caliper to the nearest 0.01 mm.
3. Alternate the layers of the specimens to be tested with the paper towels, starting and ending with two paper towels. The choice of paper towel does not matter and is present to prevent "nesting" of the protrusions in the deformed samples. The samples should be oriented so the edges of each of the specimens and each of the paper towels are relatively aligned, and the protrusions in the specimens are all oriented the same direction.
4. Place the stack of samples into a 40° C. and 10% to 30% relative humidity oven and place a weight on top of the stack. The weight must be larger than the foot of the thickness tester. To simulate high pressures or low in-bag stack heights, apply 35 kPa (e.g. 17.5 kg weight over a 70×70 mm area). To simulate low pressures or high in-bag stack heights, apply 7 kPa (e.g. 3.45 kg weight over a 70×70 mm area), 4 kPa (e.g., 1.9 kg weight over a 70×70 mm area) or 1 kPa (e.g., 0.49 kg weight over a 70×70 mm area).

5. Leave the samples in the oven for 15 hours. After the time period has elapsed, remove the weight from the samples and remove the samples from the oven.
6. Within 30 minutes of removing the samples from the oven, measure the post-compression caliper as directed in step 2 above, making sure to maintain the same order in which the pre-compression caliper was recorded. Record the post-compression caliper of each of the 10 specimens to the nearest 0.01 mm.
7. Let the samples rest at 23±2° C. and at 10 to 30% relative humidity for 24 hours without any weight on them.
8. After 24 hours, measure the post-recovery caliper of each of the 6 specimens as directed in step 2 above, making sure to maintain the same order in which the pre-compression and post-compression calipers were recorded. Record the post-recovery caliper of each of the 6 specimens to the nearest 0.01 mm. Calculate the amount of caliper recovery by subtracting the post-compression caliper from the post-recovery caliper and record to the nearest 0.01 mm.
9. If desired, an average of the 6 specimens can be calculated for the pre-compression, post-compression and post-recovery calipers.

Opacity Test Method:

Opacity is a measure of the capacity of a material to obscure the background behind it. The value for opacity is obtained by dividing the reflectance obtained with a black backing (RB) for the material, by the reflectance obtained for the same material with a white background (WB). This is called the contrast ratio (CR) method.

$$\% \text{ Opacity} = \frac{RB}{RW} \times 100$$

Using a Hunter Colorimeter set to XYZ color scale, opacity is defined as:

$$\% \text{ Opacity} = \frac{Y \text{ reading over black plate}}{Y \text{ reading over white plate}} \times 100$$

Sample Preparation

A specimen of suitable size (generally about 10 cm square) is cut for analysis. The specimen must be free of creases, wrinkles, tears and other obvious defects.

If the opacity of the material is affected by temperature and/or humidity, the specimens must be conditioned under standard conditions (23° C. (±2° C.); 10% to 30% Relative Humidity) until equilibrium is reached, and measured under those conditions.

If the topsheet material is treated with one or more surfactants, the material used for the test is the surfactant-treated topsheet material.

Equipment

Hunter Labscan® XE available from Hunter Associates Laboratory, Inc., USA. The instrument is configured as follows:

Geometry 45°/0°
Color Scale XYZ
Illuminant D65
Observer 10°

The colorimeter is calibrated using the standard gloss black glass and gloss white tile supplied with the instrument according to the manufacturer's instructions.

Test Procedure

The specimen is placed on the white tile and inserted into the colorimeter according to the manufacturer's instructions. The machine direction of the specimen should be aligned front-to-back in the instrument. The Y reading is recorded to the nearest 0.1 unit. The procedure is repeated using the black standard plate instead of the white standard tile.

Ten specimens are measured and the opacity results are averaged to obtain the % opacity value for the material.

$$\% \text{ Opacity} = \frac{\text{``}Y\text{''} \text{ on black plate}}{\text{``}Y\text{''} \text{ on white plate}} \times 100$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a wearer-facing topsheet, a backsheet and an absorbent core disposed between the topsheet and the backsheet, the article comprising a three-dimensional substrate having a wearer-facing first surface, a second surface and land areas and comprising three-dimensional protrusions extending outward from the second surface of the three-dimensional substrate, wherein the three-dimensional protrusions are surrounded by the land areas;

wherein the three-dimensional substrate is a laminate comprising at least first and second layers in a face to face relationship, wherein the first layer is closest to and/or forms the wearer-facing first surface and the second layer is a wet laid tissue layer facing outward from the second surface of the three-dimensional substrate, wherein the tissue layer comprises at least 70% pulp fibers by weight of the tissue layer; wherein the first and second layers have been mechanically deformed together to form the three-dimensional protrusions; and
wherein a majority of the three-dimensional protrusions comprise holes formed in the tissue layer at distal portions of the protrusions, and no holes formed in the first layer at said distal portions of the protrusions.

2. The three-dimensional substrate according to claim 1, wherein the first layer is a liquid permeable topsheet or an acquisition layer.

3. The three-dimensional substrate according to claim 1, wherein the three-dimensional substrate comprises at least two layers comprising fibers, wherein the three-dimensional protrusions are formed from the fibers of at least two layers of the three-dimensional substrate, wherein a majority of the three-dimensional protrusions comprise a base forming an opening, an opposed distal portion, and one or more side walls between the bases and the distal portions of the majority of the three-dimensional protrusions, and wherein the base, distal portion and the one or more side walls are formed by fibers such that the majority of the three-dimensional protrusions has only one opening at the base.

4. The three-dimensional substrate according to claim 1, wherein the majority of the three-dimensional protrusions comprises an inside void volume.

5. The three-dimensional substrate according to Claim 1, wherein at least 70% to 100% of the three-dimensional protrusions have holes formed in the tissue layer at the distal portions of the three-dimensional protrusions.

6. The three-dimensional substrate according to claim 1, wherein the three-dimensional substrate consists of two layers, and wherein the first layer is the liquid permeable topsheet to form a topsheet/tissue layer laminate.

7. The three-dimensional substrate according to claim 1, wherein the three-dimensional substrate consists of two layers, and wherein the first layer is the acquisition layer to form an acquisition layer/tissue layer laminate.

8. The three-dimensional substrate according to claim 1, wherein the three-dimensional substrate consists of three layers, wherein the first layer is the acquisition layer and the third layer is the liquid permeable topsheet, to form topsheet/acquisition layer/tissue layer laminate, and wherein the layers of the laminate are in a face to face relationship and the first layer is in between the third layer and the second layer.

9. The three-dimensional substrate according to claim 8, wherein the first layer and the third layer are nonwoven webs.

10. The three-dimensional substrate according to claim 1, wherein the tissue layer as a precursor comprises a continuous network region and a plurality of discrete zones wherein the discrete zones are dispersed throughout the continuous network region.

11. The three-dimensional substrate according to claim 10, wherein the tissue layer as a precursor further comprises a plurality of transition regions, and wherein the transition regions are positioned intermediate the continuous network region and at least some of the plurality of discrete zones.

12. The three-dimensional substrate according to claim 1, wherein the tissue layer comprises at least 90% pulp fibers by weight of the tissue layer.

13. The absorbent article of claim 1, comprising:
a longitudinal axis; and
a transversal axis perpendicular to the longitudinal axis;
wherein the absorbent core is located between the three-dimensional substrate and the backsheet.

14. The absorbent article according to claim 13, wherein the three-dimensional substrate consists of three layers, wherein the first layer is the acquisition layer, the second layer is the tissue layer and the third layer is the liquid permeable topsheet, to form topsheet/acquisition layer/tissue layer laminate, and wherein a width of the acquisition layer and the tissue layer in a direction parallel to the transversal axis is less than a width of the topsheet in a direction parallel to the transversal axis of the article.

15. The absorbent article according to claim 13, comprising a distribution layer having a dry-laid fibrous structure.

16. The absorbent article according to claim 13, wherein the absorbent core comprises an absorbent material, and wherein the absorbent material comprises from 80% to 100% of superabsorbent polymers by total weight of the absorbent material.

* * * * *